(12) United States Patent
Greenwald et al.

(10) Patent No.: US 8,618,124 B2
(45) Date of Patent: *Dec. 31, 2013

(54) HETEROBIFUNCTIONAL POLYMERIC BIOCONJUGATES

(75) Inventors: Richard B. Greenwald, Somerset, NJ (US); Hong Zhao, Edison, NJ (US)

(73) Assignee: Belrose Pharma, Inc., Princeton, NJ (US)

( * ) Notice: Subject to any disclaimer, the term of this patent is extended or adjusted under 35 U.S.C. 154(b) by 1005 days.

This patent is subject to a terminal disclaimer.

(21) Appl. No.: 11/861,091

(22) Filed: Sep. 25, 2007

(65) Prior Publication Data

US 2008/0076792 A1    Mar. 27, 2008

Related U.S. Application Data

(62) Division of application No. 10/394,393, filed on Mar. 21, 2003, now Pat. No. 7,332,164.

(51) Int. Cl.
| | | |
|---|---|---|
| *A61K 31/44* | (2006.01) | |
| *C07D 491/22* | (2006.01) | |
| *C07D 498/22* | (2006.01) | |
| *C07C 269/00* | (2006.01) | |
| *C07C 271/10* | (2006.01) | |
| *C07C 271/18* | (2006.01) | |

(52) U.S. Cl.
USPC .............. 514/283; 514/483; 546/48; 560/158

(58) Field of Classification Search
USPC ....................... 514/283, 483; 546/48; 560/158
See application file for complete search history.

(56) References Cited

U.S. PATENT DOCUMENTS

| | | | |
|---|---|---|---|
| 5,498,615 | A | 3/1996 | Kim et al. |
| 6,046,305 | A | 4/2000 | Choi |
| 6,113,906 | A | 9/2000 | Greenwald et al. |
| 6,180,095 | B1 | 1/2001 | Greenwald et al. |
| 6,251,382 | B1 | 6/2001 | Greenwald et al. |

(Continued)

FOREIGN PATENT DOCUMENTS

| | | |
|---|---|---|
| EP | 0903152 A2 | 3/1999 |
| JP | 2000-302864 | 10/2000 |
| WO | 9930727 | 6/1999 |
| WO | 0174402 A2 | 10/2001 |

OTHER PUBLICATIONS

Krause et al. (Proc. Natl. Acad. Sci. 1990, vol. 87, pp. 1471-1475.).*

(Continued)

*Primary Examiner* — Noble Jarrell
*Assistant Examiner* — Valerie Rodriguez-Garcia
(74) *Attorney, Agent, or Firm* — Lucas & Mercanti, LLP

(57) ABSTRACT

Heterobifunctional polymeric prodrug platforms for delivering biologically active compounds, including proteins, monoclonal antibodies and the like are disclosed. One preferred compound is

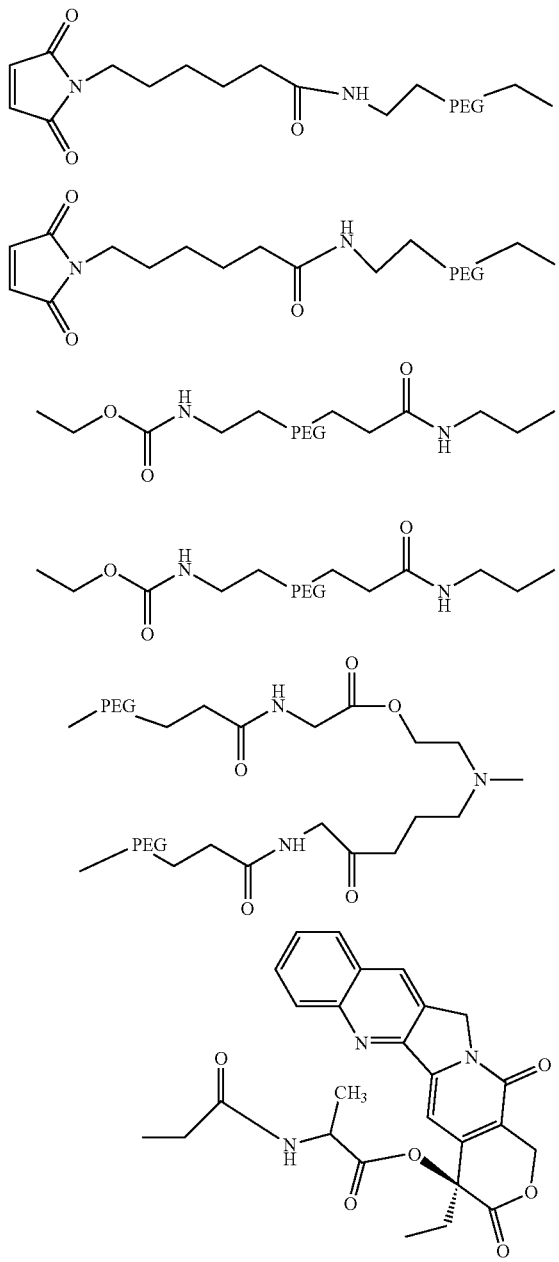

Methods of making and using the compounds and conjugates described herein are also provided.

5 Claims, 9 Drawing Sheets

(56) References Cited

U.S. PATENT DOCUMENTS

| | | | |
|---|---|---|---|
| 6,320,017 | B1 | 11/2001 | Ansell |
| 6,669,951 | B2 | 12/2003 | Rothbard et al. |
| 6,774,180 | B2 | 8/2004 | Kozlowski et al. |
| 6,936,597 | B2 | 8/2005 | Greenwald et al. |
| 7,087,229 | B2 * | 8/2006 | Zhao et al. ............ 424/179.1 |
| 7,122,189 | B2 * | 10/2006 | Zhao et al. ............ 424/179.1 |
| 7,595,304 | B2 * | 9/2009 | Zhao et al. ............ 514/44 R |
| 2002/0072573 | A1 | 6/2002 | Bentley et al. |
| 2002/0082345 | A1 | 6/2002 | Kozlowski et al. |
| 2002/0127198 | A1 | 9/2002 | Rothbard et al. |
| 2002/0161052 | A1 | 10/2002 | Choe et al. |
| 2002/0183259 | A1 | 12/2002 | Choe et al. |
| 2002/0197261 | A1 | 12/2002 | Li et al. |
| 2004/0136947 | A1 | 7/2004 | Zhao et al. |
| 2004/0142858 | A1 | 7/2004 | Greenwald et al. |

OTHER PUBLICATIONS

Pathak, A.K., Chem 534: Advance Organic Chemistry-Synthetic Aspects. web document <http://www.wiu.edu/users/michem/Pathak/CHEM%20534.htm> 6 pages, accessed Jun. 8, 2006.

Shearwater Corporation Catalog, 17 pages, 2001.

Bettinger, T., et al., "Convenient Polymer-Supported Synthetic Route to Heterobifunctional . . . ", Bioconjugate Chem, 9: 842-846, 1998.

Suzawa, T., "Enhanced Tumor Cell Selectivity of Adriamycin-Monoclonal Antibody Conjugate . . . ", Journal of Controlled Release, 79: 229-242, 2002.

Greenwald, R.B., et al., "Drug Delivery Systems based on Trimethyl Lock Lactonization . . . ", J. Med. Chem., 43: 475-487, 2000.

Nakao, K., et al., "Rat Brain Natriuretic Peptide. Isolation from Rat Heart and Tissue Distribution", Hypertension, 15: 774-778, 1990.

Zalipsky S. et al., "Poly(ethylene glycol)-grafted liposomes with oligopeptide or oligosaccharide ligands appended to the termini of the polymer chains," Bioconjugate Chemistry, Jan. 1997, vol. 8, No. 2, pp. 111-118.

Suido H. et al., "Characterization of N-CBZ-Glycyl-Glycyl-Arginyl Peptidase and Glycyl-Prolyl Peptidase of Bacteroides Gingivalis," Journal of Periodontal Research, Jan. 1987, vol. 22, No. 5, pp. 412-418.

Choe Y H. et al., "Anticancer drug delivery systems: multi-loaded N<4>-acyl poly(ethylene glycol) prodrugs of ara-C.—II. Efficacy in ascites and solid tumors," Journal of Controlled Release, Feb. 2002, vol. 79, No. 1-3, pp. 55-70.

Torchlin V. et al., "p-Nitrophenylcarbonyl-PEG-PE-liposomes: fast and simple attachment of specific ligands, including monoclonal antibodies, to distal ends of PEG chains via p-nitrophenylcarbonyl groups," Biochimica et Biophysical Acta. Biomembranes, Apr. 2001, vol. 1511, No. 2, pp. 397-411.

Yokota T. et al., "Rapid tumor penetration of a single-chain Fv and comparison with other immunoglobulin forms," Cancer Research, Jun. 1992, vol. 52, No. 12, pp. 3402-3408.

Johnson D A et al., "Anti-Tumour Activity of CC49-Doxorubicin Immunoconjugates," Anticancer Research, 1995, vol. 15, No. 4, pp. 1387-1394.

European Search Report EP 04720371.6 dated Mar. 1, 2011.

* cited by examiner

HETEROBIFUNCTIONAL POLYMERIC BIOCONJUGATES

CROSS-REFERENCE TO RELATED APPLICATION

This application is a divisional application of U.S. patent application Ser. No. 10/394,393 filed Mar. 21, 2003, the contents of which are incorporated herein by reference.

TECHNICAL FIELD

The present invention relates to the synthesis of high molecular weight heterobifunctional polymeric conjugates useful in the targeting and delivery of therapeutic agents. Methods of making and using the conjugates are also disclosed.

BACKGROUND OF THE INVENTION

Targeting and drug delivery of therapeutics is becoming increasingly important especially with the use of cytotoxics in the treatment of cancer. A number of methods have been used to selectively target tumors with therapeutic agents to treat cancers in humans and other animals. Targeting moieties such as monoclonal antibodies (mAb) or their fragments have been conjugated to linear polymers via their side chain functional groups. However, this approach usually results in reduced receptor binding affinity either due to changes in the chemical properties of the antibodies or due to folded configuration of polymers that imbed the targeting moiety in the random coiled structure. Ideally, a new conjugate would encompass both a targeting functionality as well as a therapeutic value.

Recently, heterobifunctional polymeric conjugates having a targeting functional group on one end and a therapeutic moiety (e.g. a chemotherapeutic drug) on the opposite end has been disclosed, see US Patent Application 2002/0197261A1. The polymer conjugates employed have a polymeric spacer bonded to a polymeric carrier containing multiple side-chain functional groups that allow the attachment of multiple drug, molecules (e.g. poly(1-glutamic acid)) on one end, with the other end of the polymeric spacer bonded to a targeting moiety. However, the molecular weight of the polymeric spacer portion is considerably low.

Methods of preparing higher molecular weight heterobifunctional polymer constructs have been disclosed, see US Patent Application 2002/0072573A1. However, these methods involve the polymerization of monomers which in itself is not ideal due to undesirable polymer dispersity. Other previous methods have involved anionic ethoxylation and difficult purification steps. Attempting to achieve high molecular weight polymer substrates using the techniques above has resulted in poor quality and poor yield of desired product.

Due to the inadequacies of the present methods there exists a need for improved methods of making high molecular weight heterobifunctional polymer substrates that produce high yield and high purity substrates at the same time retaining low polymer dispersity. It would also be desirable to provide compounds incorporating heterobifunctional polymer substrates as a means of targeting and delivering therapeutically active compounds. The present invention addresses these needs.

SUMMARY OF THE INVENTION

In one aspect of the invention there are provided compounds of the formula (I):

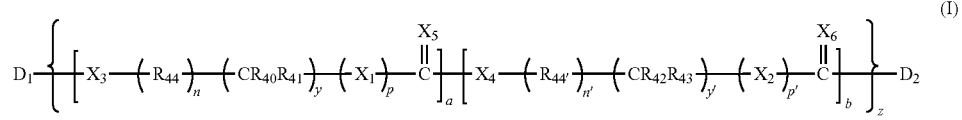

wherein:
$X_1$-$X_6$ are independently O, S or $NR_1$;
$R_{44}$ and $R_{44'}$ are independently selected polyalkylene oxides;
$R_1$ is selected from among hydrogen, $C_{1-6}$ alkyls, $C_{3-12}$ branched alkyls, $C_{3-8}$ cycloalkyls, $C_{1-6}$ substituted alkyls, aralkyls, and $C_{3-8}$ substituted cycloalkyls;
$R_{40-43}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
y, and y' are independently zero or a positive integer;
p and p' are independently zero or one;
n and n' are independently one or a positive integer;
a and b are independently zero or a positive integer, provided that a+b is greater than or equal to two;
z is 1 or a positive integer;
$D_1$ and $D_2$ are independently selected from among B, leaving groups, activating groups, OH and terminal groups; and
B is selected from among biologically active moieties, diagnostic agents and OH.

In a preferred embodiment, $X_1$-$X_6$ are independently Q or $NR_1$, $R_1$ is hydrogen, a and b are independently selected integers from 1 to about 20, y and y' are independently 0, 1 or 2, p and p' are each 1, $D_1$ and $D_2$ are independently selected from among leaving groups and terminal groups and B, wherein B is a biologically active moiety such as, a drug, an amino or hydroxyl-containing residue, a diagnostic agent such as a dye, chelating agent or isotope labeled compound, a leaving group or activating group.

For purposes of die present invention, the term "residue" shall be understood to mean that portion of a biologically active compound which remains after it has undergone a substitution reaction in which the prodrug carrier has been attached.

For purposes of the present invention, the term "alkyl" shall be understood to include straight, branched, substituted $C_{1-12}$ alkyls, $C_{3-8}$ cycloalkyls or substituted cycloalkyls, etc.

Some of the chief advantages of the present invention include novel high molecular weight heterobifunctional polymeric conjugates capable of enhancing the circulating half-life and solubility of native or unmodified molecules as well as methods of building such conjugates wherein high purity is maintained without needing a chromatography step. Another advantage of the methods of the present invention is the retention of low polymer dispersion with increasing molecular weight of the polymer conjugates. A further advantage of the present invention is that it allows for the artisan to design a drug conjugate that can have the same or different groups on either side of the polymeric portion. This advantage allows the artisan to tailor a compound to contain a delivery or targeting functionality and a therapeutic functionality within the same conjugate depending on a particular need.

Methods of making and using the compounds and conjugates described herein are also provided.

DETAILED DESCRIPTION OF THE INVENTION

A. Formula (I)

Figure 1:
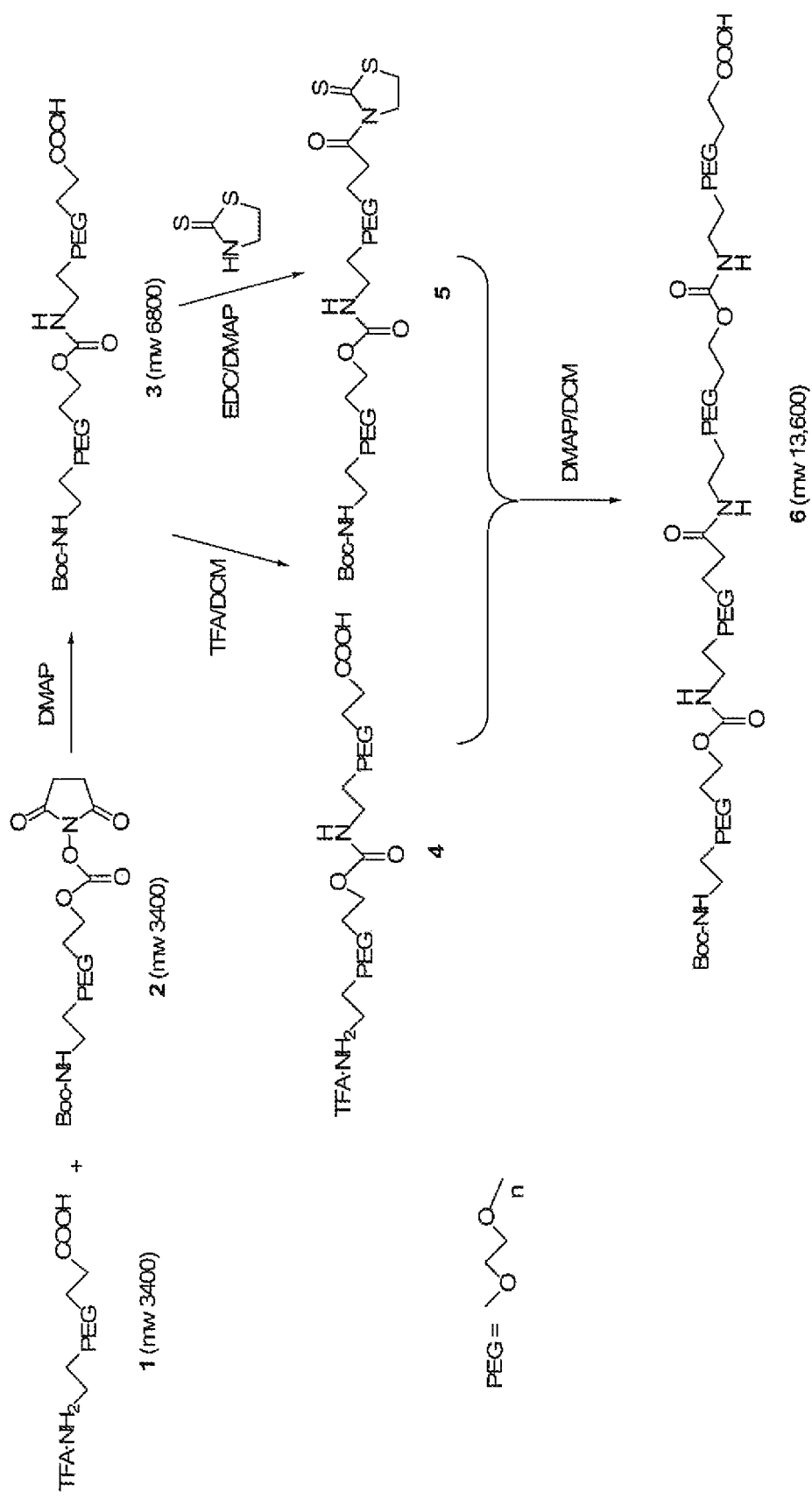
FIGS. 1 through 9 schematically illustrate methods of forming compounds of the present invention which are described in the Examples.
Figure 2:
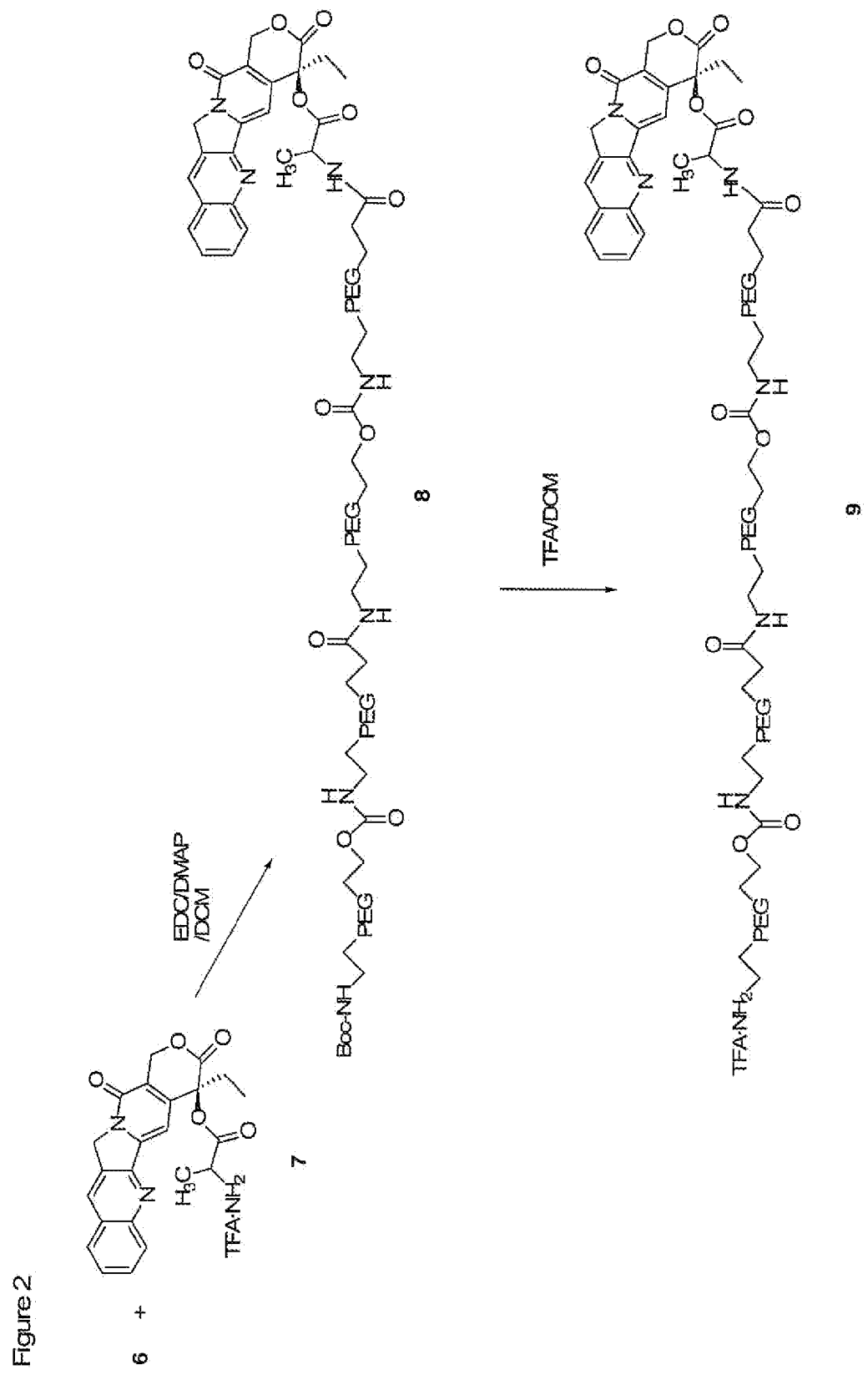
Figure 3:
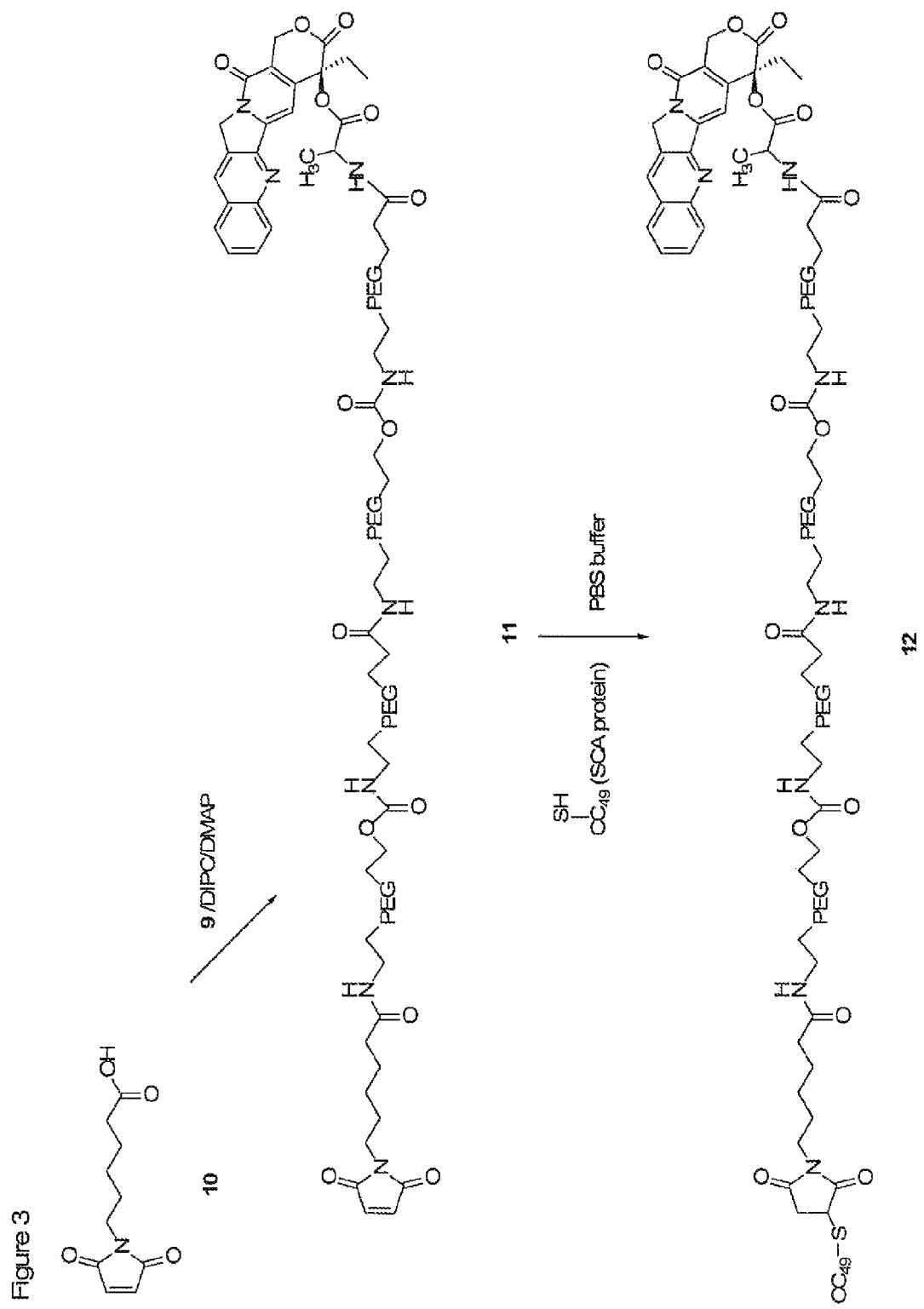
Figure 4:
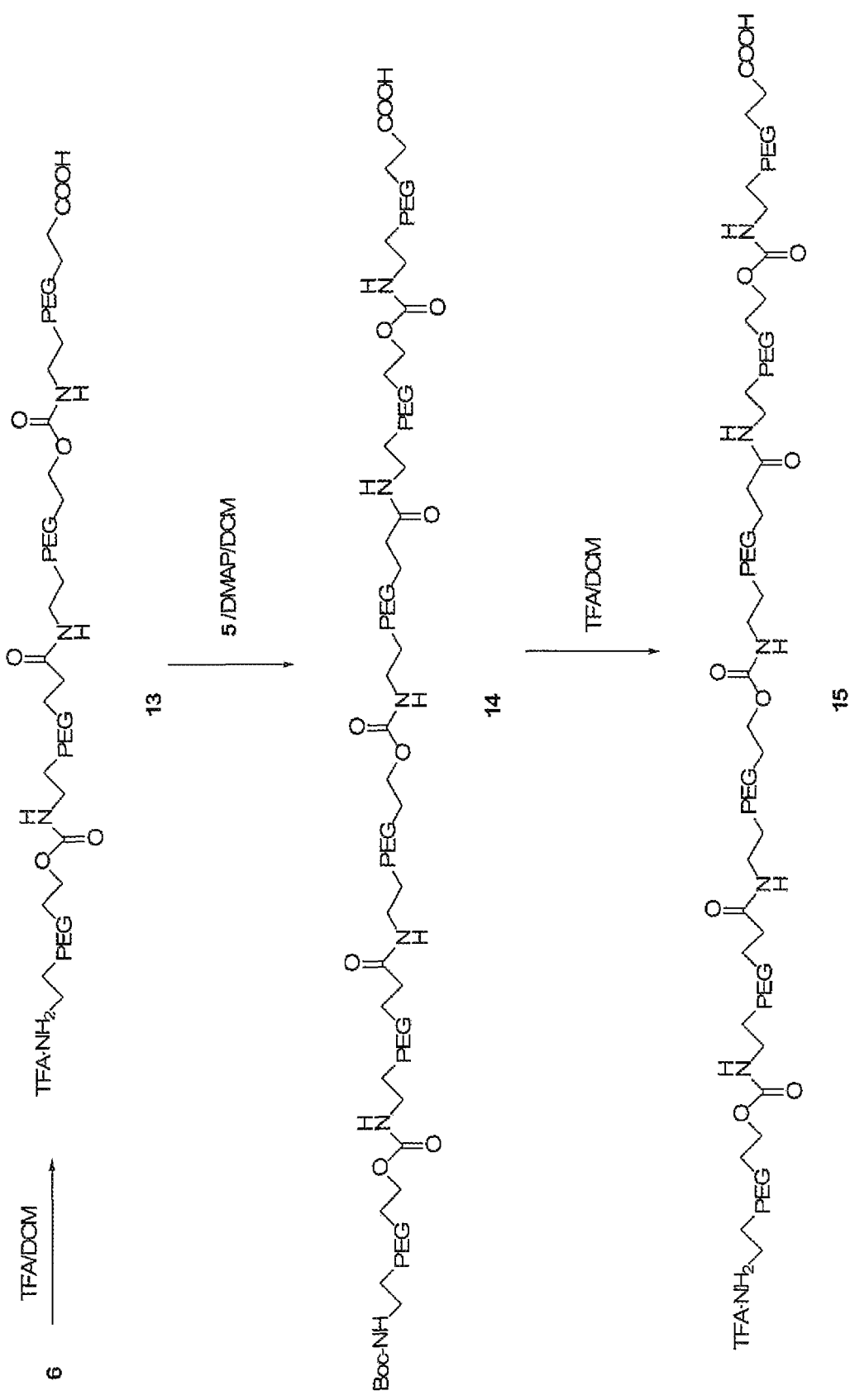
Figure 5:
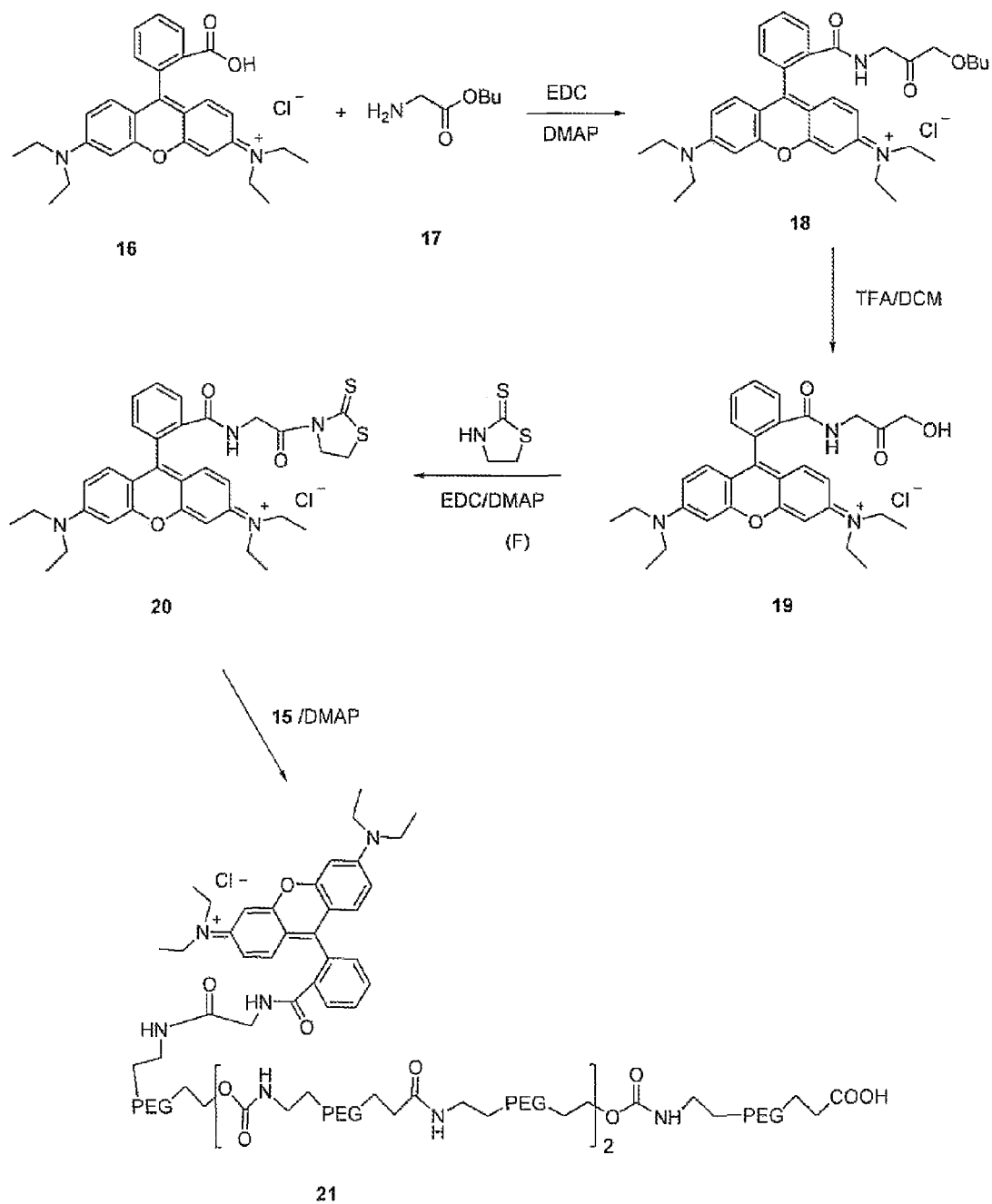
Figure 6:
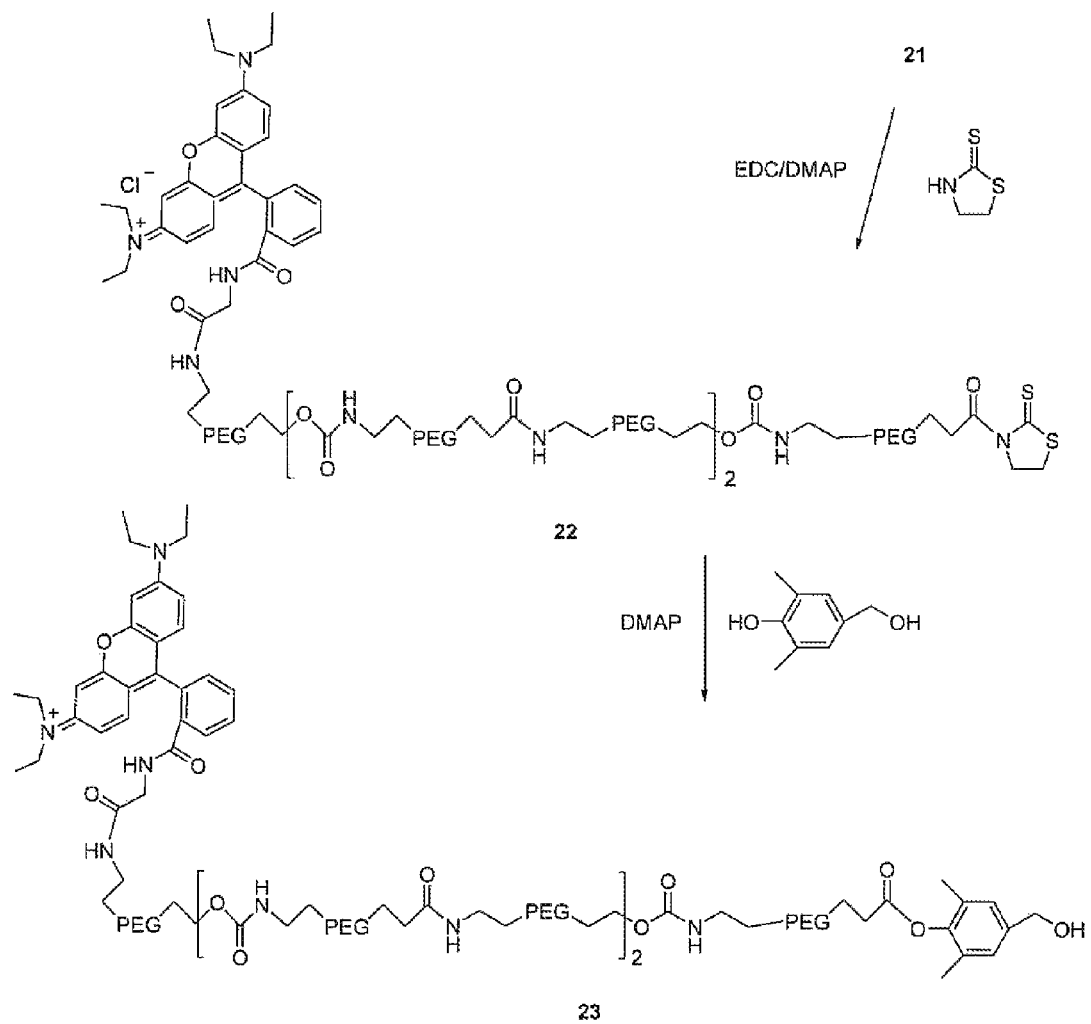
Figure 7:
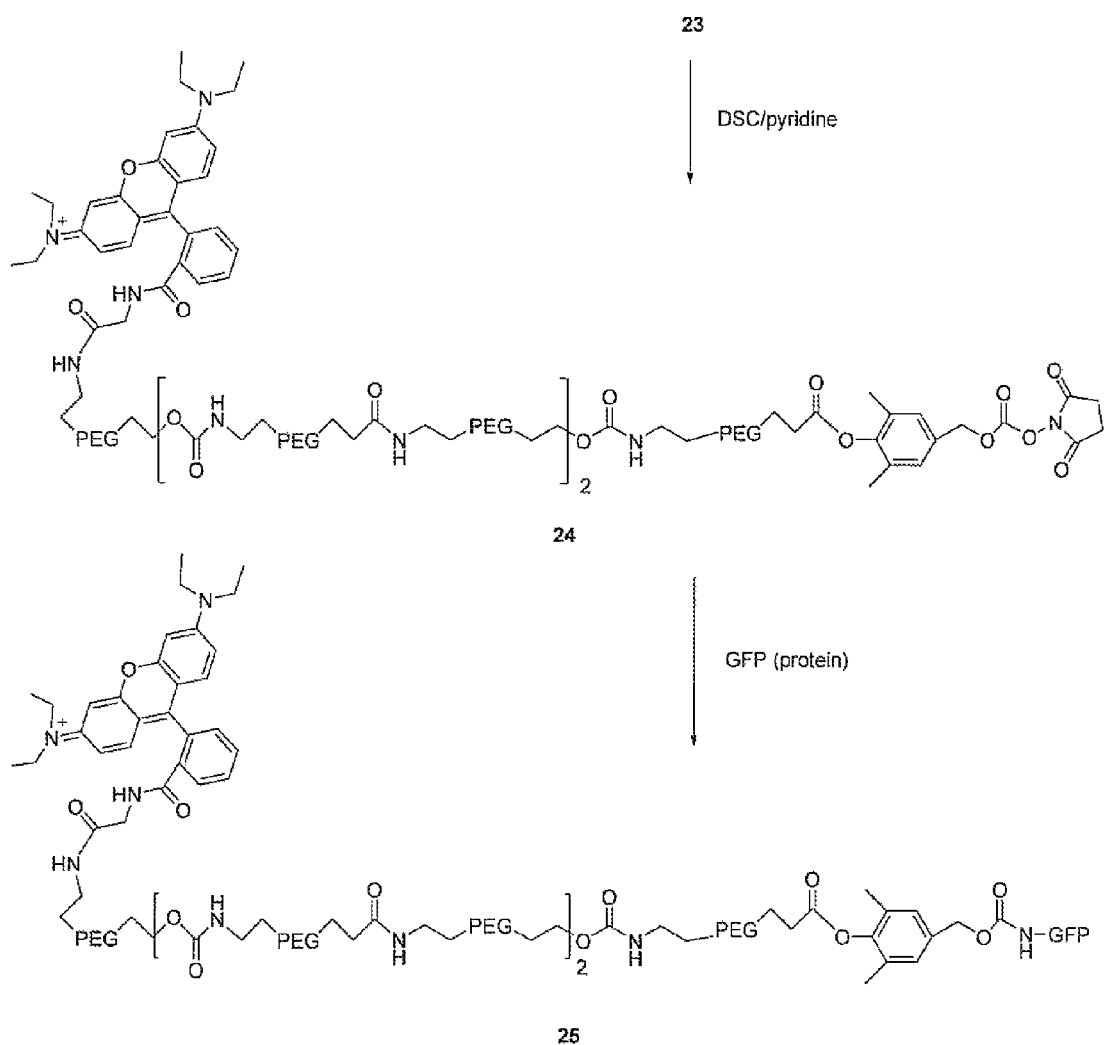
Figure 8:
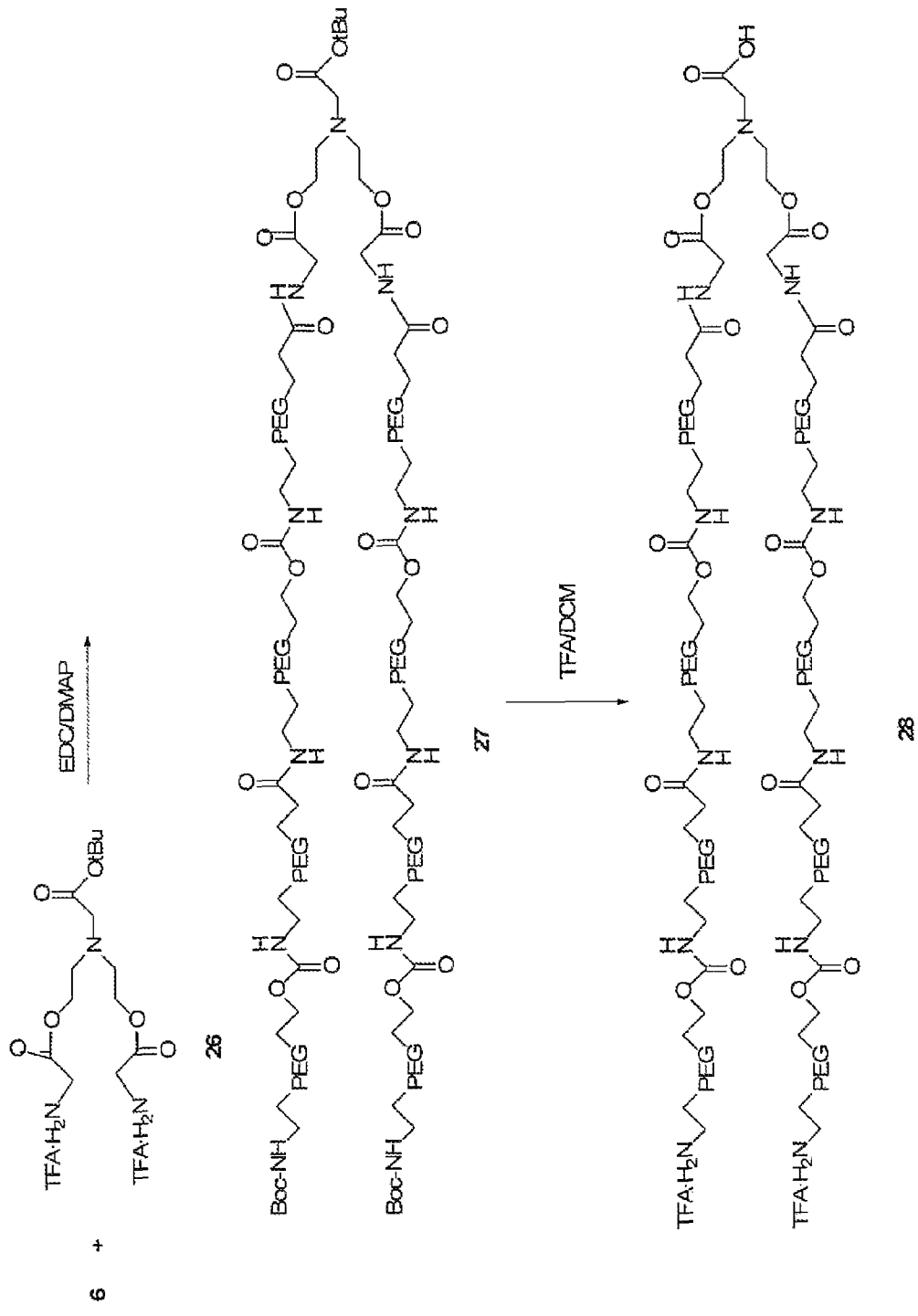
Figure 9:
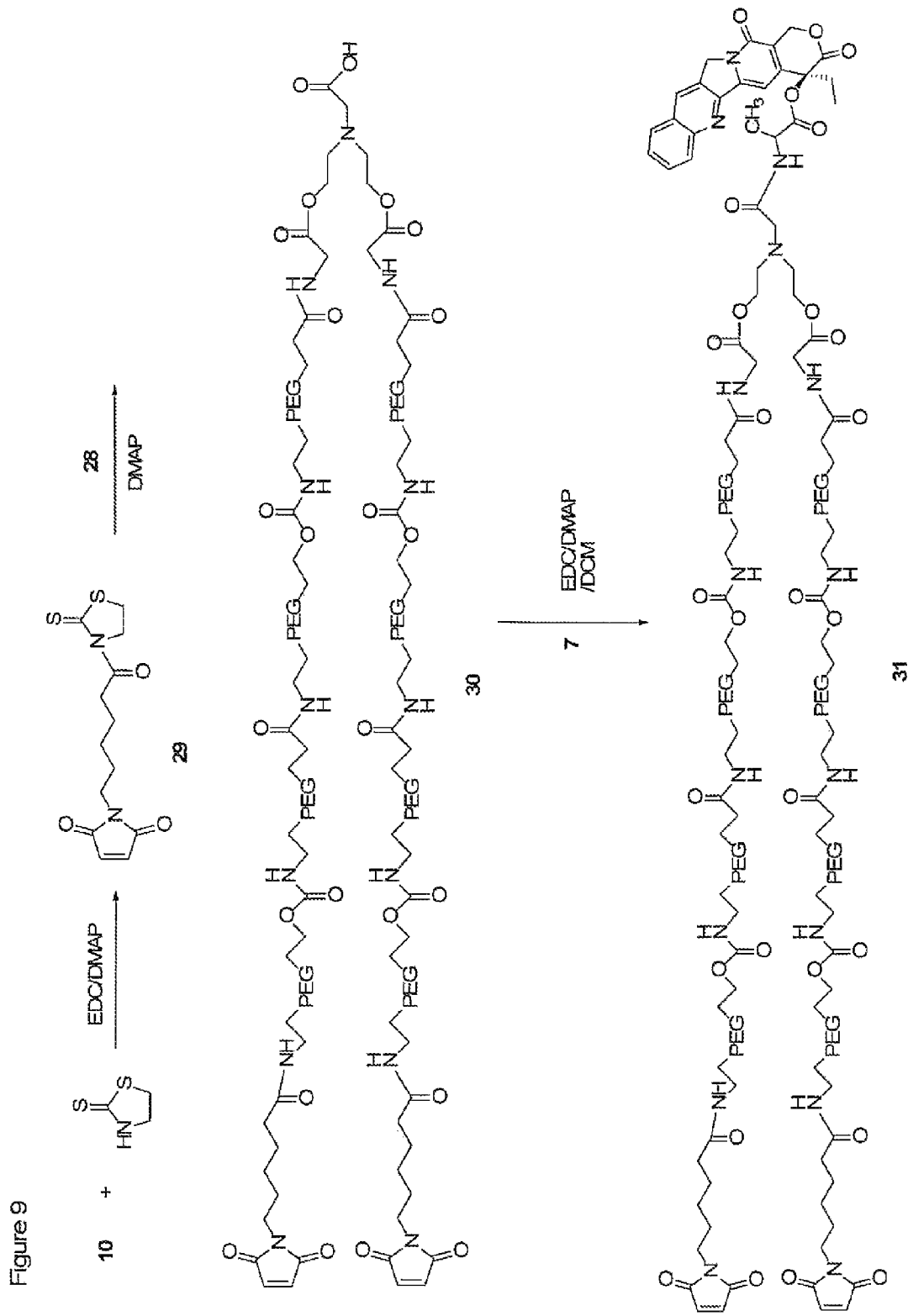

In one aspect of the invention there are provided compounds of the formula (I):

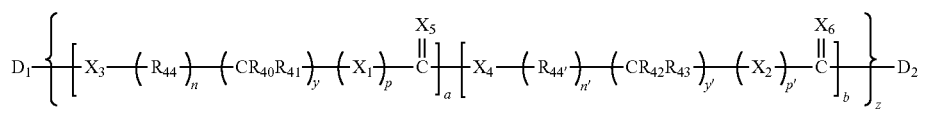

wherein:
$X_1$-$X_6$ are independently O, S or $NR_1$;
$R_{44}$ and $R_{44'}$ are independently selected polyalkylene oxides;
$R_1$ is selected from among hydrogen, $C_{1-6}$ alkyls, $C_{3-12}$ branched alkyls, $C_{3-8}$ cycloalkyls, $C_{1-6}$ substituted alkyls, aralkyls, and $C_{3-8}$ substituted cycloalkyls;
$R_{40-43}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
y, and y' are independently zero or a positive integer;
p and p' are independently zero or one;
n and n' are independently one or a positive integer;
a and b are independently zero or a positive integer, provided that a+b is greater than or equal to two;
z is 1 or a positive integer;
$D_1$ and $D_2$ are independently selected from among B, leaving groups, activating groups, OH and terminal groups; and
B is selected from among biologically active moieties, diagnostic agents and OH.

In a preferred embodiment of the compound of formula (I):
$X_1$-$X_6$ are independently O or $NR_1$;
$R_1$ is selected from among hydrogen, $C_{1-6}$ alkyls, $C_{1-6}$ heteroalkyls, aralkyls, and $C_{1-6}$ substituted alkyls;
y, and y' are independently 0 or an integer between 1 and 18;
p and p' are independently 0 or 1;
n and n' are independently selected integers between 0 and 100;
a and b are independently selected integers between 1 and 20; and
z is a positive integer.

More preferably,
$X_1$-$X_4$ are independently $NR_1$;
$X_5$-$X_6$ are each O;
$R_{44}$ and $R_{44'}$ are each —($CH_2$—$CH_2$—O)—;
$R_1$ is hydrogen or methyl;
y and y' are each 0, 1 or 2;
p and p' are each 1;
n and n' are independently selected integers between 70 and 80;
a and b are independently selected integers between 5 and 10;
z is a positive integer;

$D_1$ and $D_2$ are independently selected from among OH, halogens, targeting agents, drugs, enzymes, proteins, therapeutically active compounds, dyes, chelating agents and isotope labeled compounds.

In yet another preferred embodiment of a compound of formula (I), $D_1$ and $D_2$ are independently selected terminal groups such as:

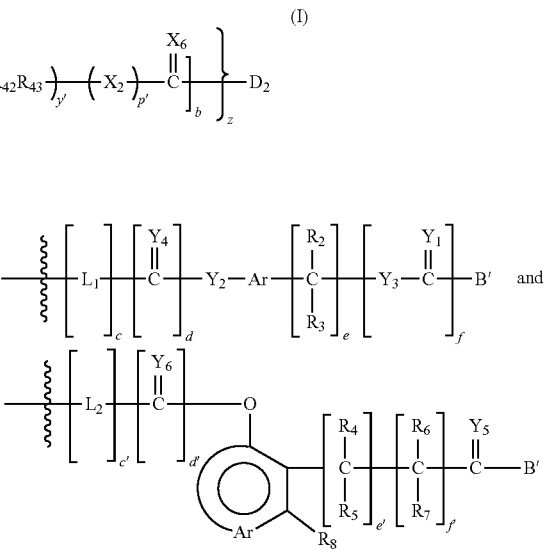

wherein:
$Y_{1-6}$ are independently O or $NR_1$;
$R_1$ is hydrogen or methyl;
$R_{2-8}$ are independently selected from among hydrogen and $C_{1-6}$ alkyls;
Ar is a moiety which forms a multi-substituted aromatic hydrocarbon or a multi-substituted heterocyclic group;
$L_{1-2}$ are independently selected bifunctional linkers;
e and f are each one;
c, c' and e' are independently zero or one;
d, f and d' are independently zero or one; and
B' is selected from among leaving groups, activating groups, OH, biologically active moieties and diagnostic agents.

In another preferred aspect of the invention, there are provided polymer conjugates of the formula (Ia):

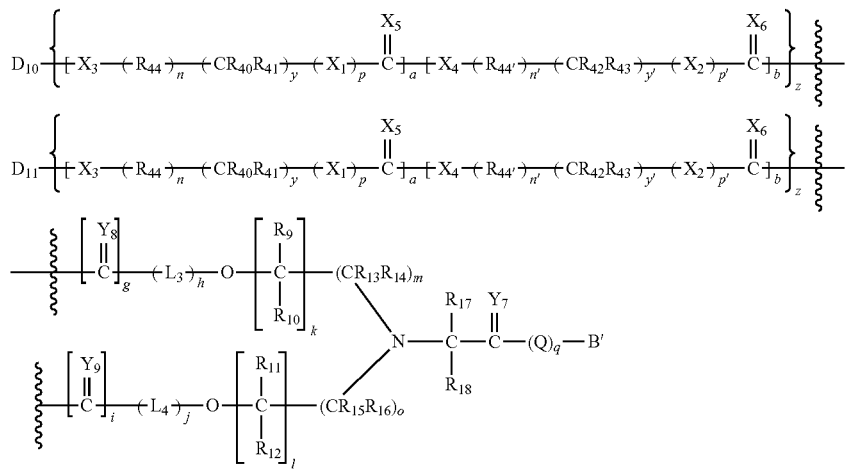

wherein:

$Y_{7-9}$ are independently O or $NR_{1''}$;

$R_{1''}$ is hydrogen or methyl;

$R_{9-18}$ are independently hydrogen or $C_{1-6}$ alkyls;

$L_{3-4}$ are independently selected bifunctional linkers;

Q is selected from among moieties actively transported into a target cell, hydrophobic moieties, bifunctional linking moieties and combinations thereof;

l, k, m and o are independently positive integers;

j and h are independently zero or one;

g, and i are each one;

q is zero or one;

B' is selected from among leaving groups, activating groups, OH, biologically active moieties and diagnostic agents;

$D_{10}$ and $D_{11}$ are selected from the same group which defines $D_1$ or together form a terminal group of the formula:

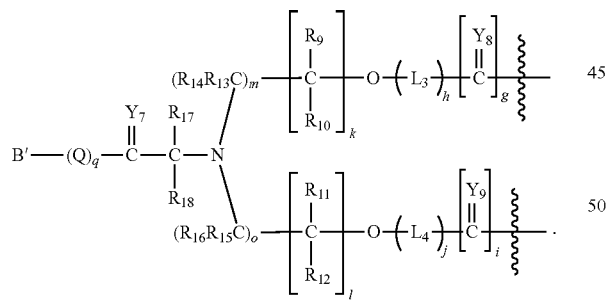

In yet another preferred aspect of the invention, $D_1$ and $D_2$ are independently selected terminal groups such as:

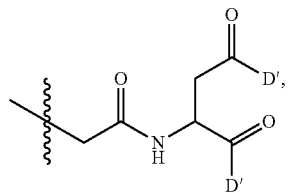

-continued

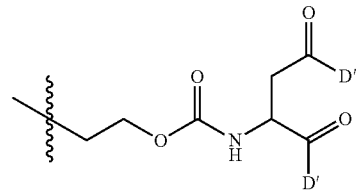

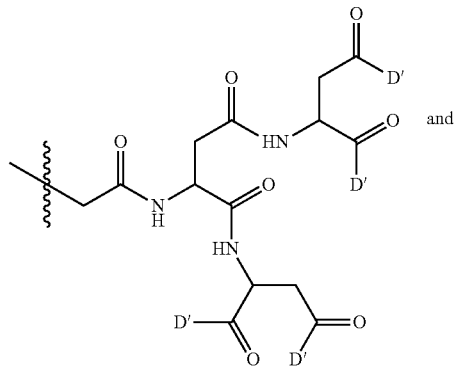

and

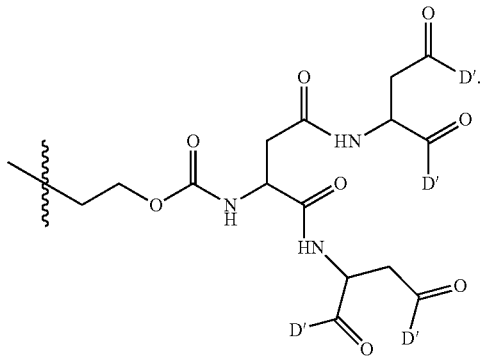

wherein D' is one of
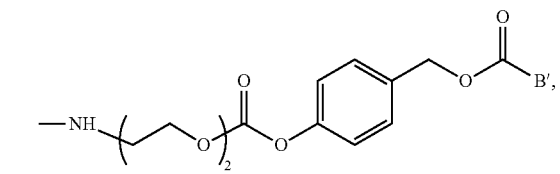
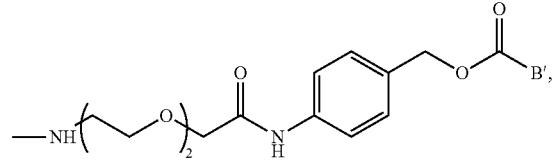
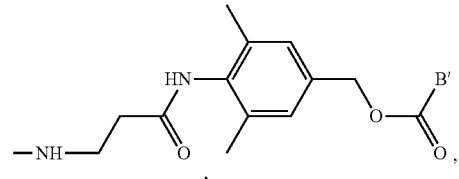
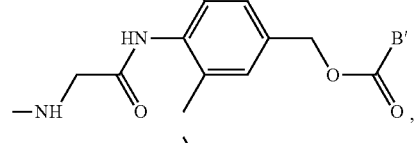
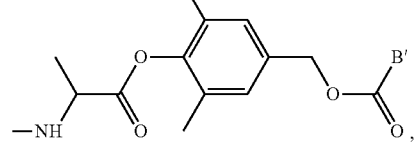
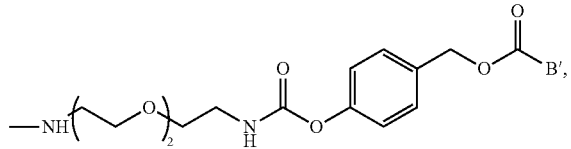
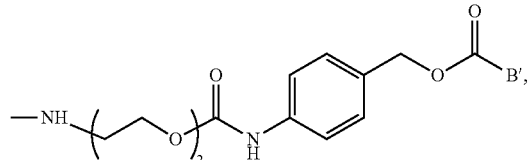
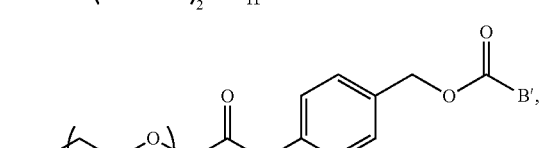
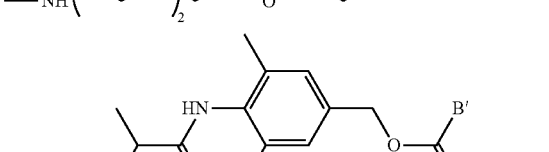
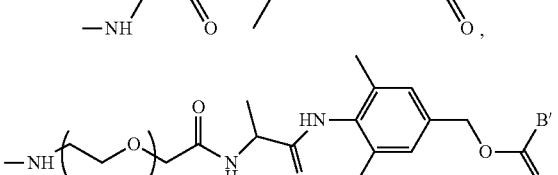
-continued
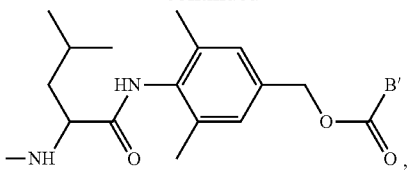
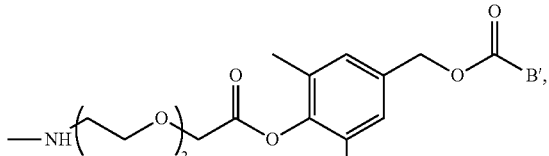
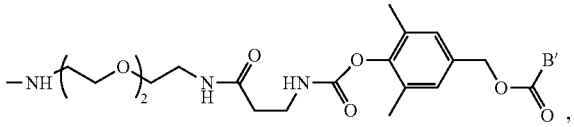
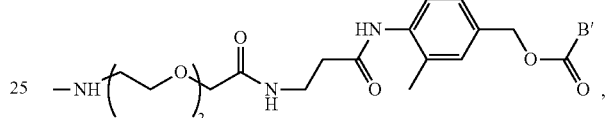
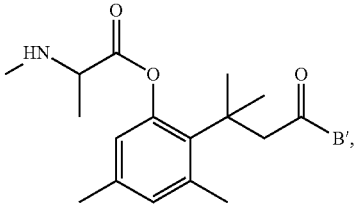
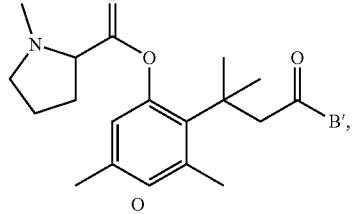
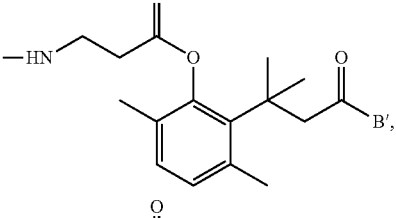
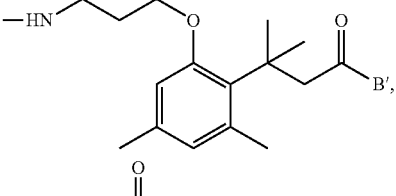
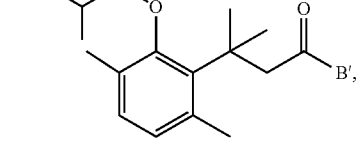

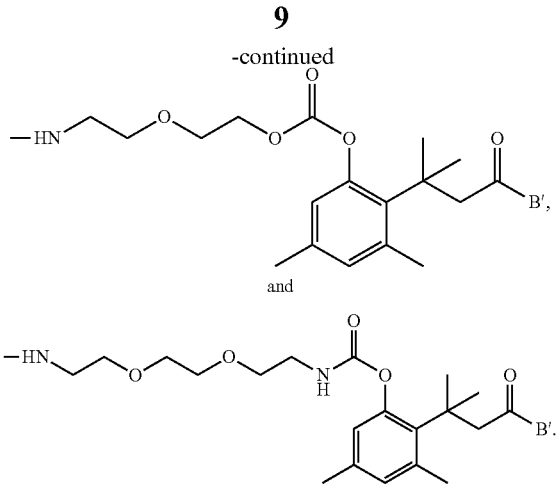

where B' is selected from among leaving groups, activating groups, OH, biologically active moieties and diagnostic agents.

B. Linker Moieties $L_{1-4}$

As shown above, the invention may include the bifunctional linking moieties $L_1$-$L_4$. Preferably, $L_1$-$L_4$ are independently selected from among the non-limiting list:

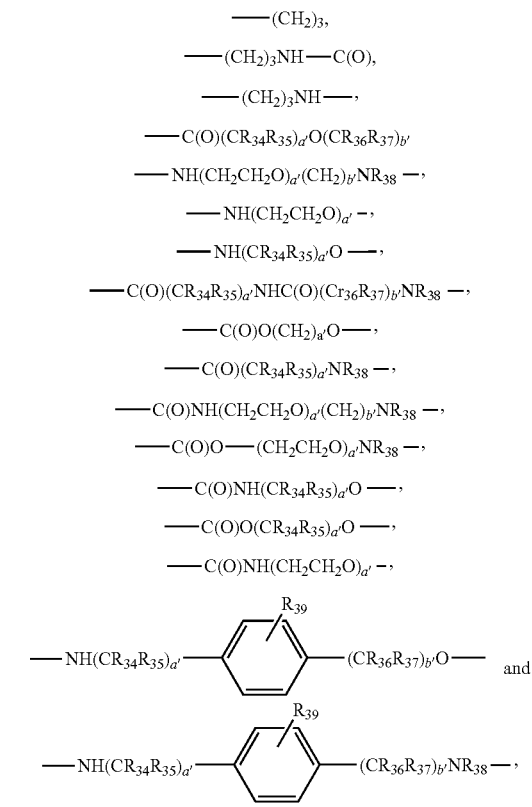

wherein:

$R_{34}$-$R_{38}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{39}$ is selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, $NO_2$, haloalkyl and halogens;

a' and b' are independently selected positive integers.

C. Description of the Ar Moiety

In certain aspects of the invention, it can be seen that the Ar moiety is a moiety which when included in Formula (I) forms a multi-substituted aromatic hydrocarbon or a multi-substituted heterocyclic group. A key feature is that the Ar moiety is aromatic in nature. Generally, to be aromatic, the –n electrons must be shared within a "cloud" both above and below the plane of a cyclic molecule. Furthermore, the number of p electrons must satisfy the Hückel rule (4n+2). Those of ordinary skill will realize that a myriad of moieties will satisfy the aromatic requirement of the moiety for formula (I) and thus are suitable for use herein.

Some particularly preferred aromatic groups include:

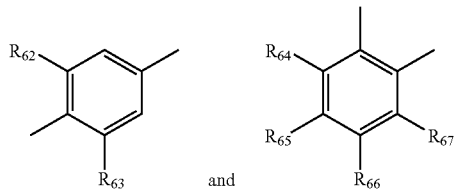

wherein $R_{62-67}$ are independently selected from the same group which defines $R_2$.

Other preferred aromatic hydrocarbon moieties include, without limitation

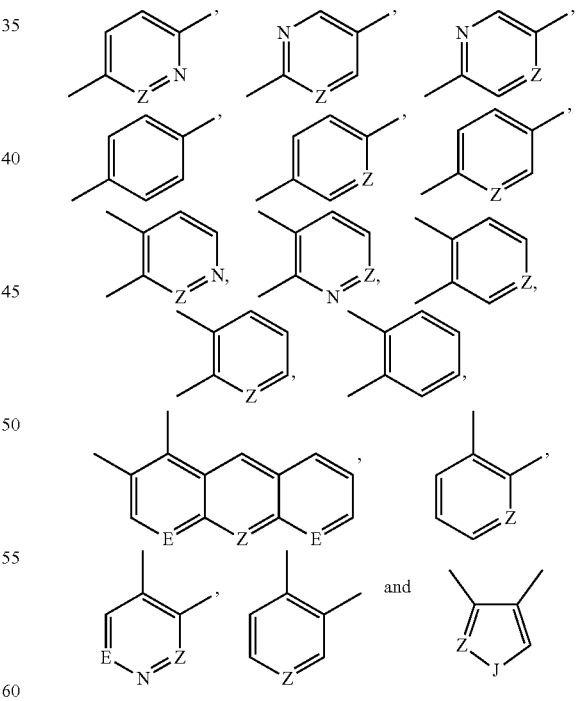

wherein Z and E are independently $CR_{68}$ or $NR_{69}$; and J is O, S or $NR_{70}$ where $R_{68-70}$ are selected from the same group at that which defines $R_2$ or a cyano, nitro, carboxyl, acyl, substituted acyl or carboxyalkyl. Isomers of the five and six-membered rings are also contemplated as well as benzo- and dibenzo-systems and their related congeners are also contemplated. It will also be appreciated by the artisan of ordinary skill that aromatic rings can optionally be substituted with hetero-atoms such as O, S, $NR_1$, etc. so long as Hückel's rule is obeyed. Furthermore, the aromatic or heterocyclic structures may optionally be substituted with halogen(s) and/or side chains as those terms are commonly understood in the art.

D. Polyalkylene Oxides

Referring to Formula (I) it can be seen that $R_{44}$ is a polymer moiety such as polyalkylene oxide. Suitable examples of such polymers include polyethylene glycols which are substantially non-antigenic. Also useful are polypropylene glycols, such as those described in commonly-assigned U.S. Pat. No. 5,643,575. Other PEG's useful in the methods of the invention are described in Shearwater Polymers, Inc. catalog "Polyethylene Glycol and Derivatives 2001". The disclosure of each is incorporated herein by reference.

Although PAO's and PEG's can vary substantially in weight average molecular weight, preferably, $R_{44}$ has a weight average molecular weight of from about 2,000 to about 136,000 Da inmost aspects of the invention. More preferably, $R_{44}$ has a weight average molecular weight of from about 3,400 to about 65,000 Da, with a weight average molecular weight of from about 3,400 to about 20,000 Da being most preferred.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

E. Formula (I) $D_1$, $D_2$ B and B' Groups

1. Leaving Groups

In those aspects of formula (I) where $D_1$, $D_2$ are independently selected leaving groups, suitable moieties include, without limitation, groups such as halogens, activated carbonates such as hydroxysuccinimidyl carbonate, carbonyl imidazole, cyclic imide thiones, isocyanates, N-para-nitrophenol, N-hydroxyphtalimide, N-hydroxybenzotriazolyl, imidazole, tosylates,

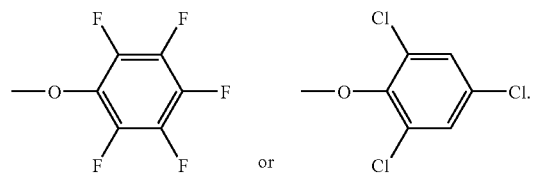

Other suitable leaving groups will be apparent to those of ordinary skill.

For purposes of the present invention, leaving groups are to be understood as those groups which are capable of reacting with a nucleophile found on the desired target, i.e. a biologically active moiety, a bifunctional spacer, intermediate, etc. The targets thus contain a group for displacement, such as $NH_2$ groups found on proteins, peptides, enzymes, naturally or chemically synthesized therapeutic molecules such as doxorubicin.

2. Activating Groups

In those aspects of formula (I) where $D_1$, $D_2$, B and B' are independently activating groups. Non-limiting examples of such functional groups include maleimidyl, vinyl, residues of vinylsulfone, hydroxy, amino, carboxy, mercapto, hydrazide, carbazate and the like. Once attached to the polymer conjugate the functional group, (e.g. maleimide), can be used to attach the polymer conjugate to a target such as the cysteine residue of a polypeptide, amino acid or peptide spacer, etc.

3. Biologically Active Moieties

In those aspects of formula (I) where $D_1$, $D_2$, B or B' are residues of an amine- or hydroxyl-containing compound. A non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, melphalan, Ara-C (cytosine arabinoside) and related anti-metabolite compounds, e.g., gemcitabine, etc. Alternatively, the moiety can be a residue of an amine- or hydroxyl-containing cardiovascular agent, anti-neoplastic agent such as camptothecin and paclitaxel, anti-infective, anti-fungal such as nystatin, fluconazole and amphotericin B, anti-anxiety agent, gastrointestinal agent, central nervous system-activating agent, analgesic, fertility agent, contraceptive agent, anti-inflammatory agent, steroidal agent, agent, etc.

In addition to the foregoing, the biologically active moiety can also be a residue of an enzyme, protein, polypeptide, single chain antigen binding proteins, (SCA's) monoclonal antibodies such as CC49, fragments thereof, etc. SCA's of monoclonal antibodies are also contemplated. Suitable proteins include but are not limited to, polypeptides, enzymes, peptides and the like having at least one available group for polymer attachment, e.g. an e-amino, cystinylthio, N-terminal amino, include materials which have physiological or pharmacological activities as well as those which are able to catalyze reactions in organic solvents.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, etc., α, β and γ interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGFα or TGFβ and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include. IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes; proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a biological polymer demonstrating in vivo bioactivity. This includes amino acid sequences, nucleic acids (DNA, RNA), peptide nucleic acids (PNA), antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino- or hydroxyl-containing compound is a biologically active compound that is suitable for medicinal or diagnostic use, in the treatment of animals, e.g., mammals, including humans, for conditions for which such treatment is desired. The foregoing list is meant to be illustrative and not limiting for the compounds which can be modified. Those of ordinary skill will realize that other such compounds/compositions can be similarly modified without undue experimentation. It is to be understood that those biologically active materials not specifically mentioned but having suitable attachment groups are also intended and are within the scope of the present invention.

The only limitations on the types of amino- or hydroxyl containing molecules suitable for inclusion herein is that there is available at least one (primary or secondary) amine- or hydroxyl- which can react and link with the polymeric conjugate and that there is not substantial loss of bioactivity after the prodrug system releases and regenerates the parent compound.

4. Diagnostic Agents

In those aspects of formula (I) where $D_1$, $D_2$, B and B' is a diagnostic agent, a non-limiting list of suitable agents includes dyes, chelating agents, and isotope labeled compounds and other labeling compounds such as Green Fluorescent Protein (GFP).

F. Q Moieties and their Function

In one aspect of the invention Q is $L_5$-C($=Y_{10}$) wherein $L_5$ is a bifunctional linker selected from among the group which defines $L_1$, $L_2$, $L_3$, and $L_4$ and $Y_{10}$ is selected from among the same groups as that which defines $Y_{1-9}$. In this aspect of the invention, the Q group servers as the linkage between the B' groups and the remainder of the polymeric conjugate.

In other aspects of the invention, Q is a moiety that is actively transported into a target cell, a hydrophobic moiety, and combinations thereof. Although Q is preferably monovalent, Q can optionally be bivalent or multivalent so to allow attachment of more than one B' group to the polymer conjugate. In order to achieve the active transport, Q can include an amino acid or peptide residue, a sugar residue, a fatty acid residue, a $C_{6-18}$ alkyl a substituted aryl, a heteroaryl, —C(=O), —C(=S) or —C(=NR$_{28}$), wherein $R_{28}$ is H, lower alkyl, etc.

This aspect of the invention is broadly based upon the principle that biologically active materials suitable for incorporation into the polymer conjugates may themselves be substances/compounds which are not active after hydrolytic release from the polymer substrate, but which will become active after undergoing a further chemical process/reaction. With this embodiment, a therapeutic or diagnostic agent, peptide, polypeptide, etc. that is delivered to the bloodstream by the polymer system, will remain inactive until entering or being actively transported into a target cell of interest, whereupon it is activated by intracellular chemistry, e.g., by an enzyme or enzyme system present in that tissue or cell.

The compounds of this aspect of the invention are prepared so that in vivo hydrolysis of the polymer-based conjugate cleaves the conjugate so as to release the active biological material (designated B' herein) into, extracellular fluid, while still linked, to the Q moiety. The biologically active materials in this aspect of the invention are preferably, but not exclusively, small molecule therapeutic and/or diagnostic agents. For example, one potential Q-B' combination is leucine-doxarubacin, another is amino acid-linked camptothecin or paclitaxel and the tissue to be treated is tumor tissue.

Without intending to be bound by any theory or hypothesis as to how the invention might operate, it is believed that, depending upon the additional moiety selected as a transport enhancer, the rate of transport of a biologically active material into tumor cells is by the delivery of a biologically active material into extracellular tissue pace, e.g., of a tissue exhibiting an EPR effect, in a protected and/or transport-enhanced form.

In a further still option, the transport enhancer (Q) is selected from among known substrates for a cell membrane transport system. Simply by way of example, cells are known to actively transport certain nutrients and endocrine factors, and the like, and such nutrients, or analogs thereof, are readily employed to enhance active transport of a biologically effective material into target cells. Examples of these nutrients include amino acid residues, peptides, e.g., short peptides ranging in size from about 2 to about 10 residues or more, simple sugars and fatty acids, endocrine factors, and the like.

Short peptides are, for example, peptides ranging from 2 to about 10, or more, amino acid residues, as mentioned supra. In this embodiment of the invention, it is believed that such peptide transport enhancers need not be hydrophobic, but are thought to function in other ways to enhance uptake and/or to protect the linked small molecule agents from premature hydrolysis in the general bloodstream. For instance, peptide transport enhancers, and other transport enhancers of similar molecular weight ranges, are thought to sterically hinder cleavage from the biologically active agent by plasma-based hydrolytic enzymes, but are then cleaved within a target cell by various peptides and/or proteases, such as capthesins.

In certain preferred aspects Q is a hydrophobic moiety. Without meaning to be bound to any theory or hypothesis as to how hydrophobicity contributes to efficacy, it is believed that a hydrophobic moiety inhibits the extracellular cleavage of the transport enhancer away from the active biological agent, by inhibiting the attack of hydrolytic enzymes, etc. present in the extracellular tissue space, e.g. in the plasma. Thus, some preferred transport enhancers include, e.g. hydrophobic amino acids such as alanine, valine, leucine, isoleucine, methionine, proline, phenylalanine, tyrosine, and tryptophane, as well as non-naturally occurring derivatives and analogs thereof, as mentioned supra.

In a further option, the transport enhancer is a hydrophobic organic moiety. Simply by way of example, the organic moiety is a $C_{6-18}$, or larger, alkyl, aryl or heteroaryl-substituted or nonsubstituted. The organic moiety transport enhancer is also contemplated to encompass and include organic functional groups including, e.g. —C(=S) and/or —C(=O).

G. Synthesis of the Heterobifunctional Polymeric Conjugates

Synthesis of specific heterobifunctional polymer compounds is set forth in the Examples. Turning now to FIG. 1 for the purpose of illustration, one preferred method includes:

1) reacting an amine protected, activated heterobifunctional PEG polymer with a heterobifunctional PEG polymer under basic coupling conditions to obtain a first intermediate, and
2) reacting the first intermediate with a suitable activating group such as NHS activated ester,
3) repeating the reaction of step 1) to obtain a second intermediate,
4) deprotecting the second intermediate, and
5) reacting the activated first intermediate with the deprotected second intermediate under coupling conditions thus achieving a high molecular weight heterobifunctional PEG conjugate.

A further method of making a polymeric conjugate according to the invention includes:

a) reacting a compound of formula (i)

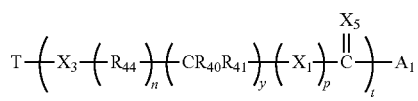

(i)

wherein:
$A_1$ is an activating group;
T is a protecting group;
$X_1$, $X_3$ and $X_5$ are independently O, S or $NR_1$;
$R_{44}$ is a polyalkylene oxide;

$R_1$ is selected from hydrogen, $C_{1-6}$ alkyls, $C_{3-12}$ branched alkyls, $C_{3-8}$ cycloalkyls, $C_{1-6}$ substituted alkyls, aralkyls, and $C_{3-8}$ substituted cycloalkyls;

$R_{40-41}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

n is 1 or a positive integer;
y is zero or a positive integer;
t is a positive integer; and
p is zero or one;

with a compound of the formula (ii):

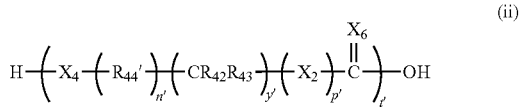

(ii)

wherein:
$X_2$, $X_4$ and $X_6$ are independently O, S or $NR_1$;
$R_{44'}$ is a polyalkylene oxide;
$R_1$ is selected from hydrogen, $C_{1-6}$ alkyls, $C_{3-12}$ branched alkyls, $C_{3-8}$ cyclo-alkyls, aralkyls, $C_{1-6}$ substituted alkyls, and $C_{3-8}$ substituted cycloalkyls;

$R_{42-43}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted-cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

n' is a positive integer;
y' is zero or appositive integer;
t' is a positive integer; and
p' is zero or one;

under sufficient conditions to form a compound of formula (iii):

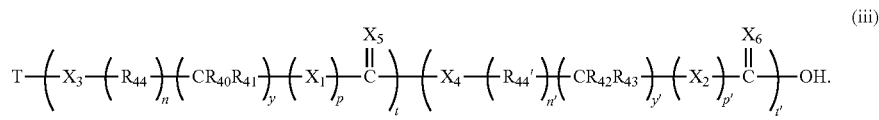

(iii)

This method can also optionally further include the step of deprotecting (iii) to provide a useful intermediate which can be used in further synthesis, activated and/or conjugated to a drug, etc. Alternatively, the method can further include the step of reacting (iii) with an activating agent under sufficient conditions to form a compound of formula (iv):

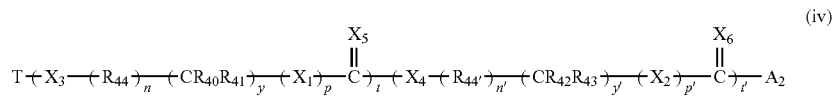

(iv)

wherein $A_2$ is an activating group and all other variables are as defined above.

In still further aspects, the method can include the step of converting the amino protecting group (T) of formula (iv) to an activating group under sufficient conditions to form a compound of formula (v):

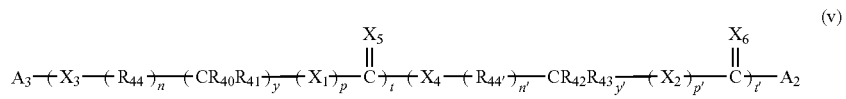
(v)

wherein $A_3$ is an activating group.

Once a compound of formula (v) is formed, it can be reacted with a biologically active moiety, diagnostic agent or a terminal group under sufficient conditions to form a compound of formula (vi):

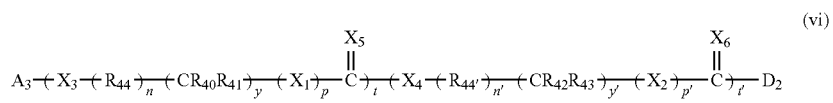
(vi)

wherein $D_2$ is a biologically active moiety, diagnostic agent or terminal group and all other variables are as defined above.

A non-limiting list of suitable coupling agents include 1,3-diisopropyl-carbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as tetrahydrofuran (THF), acetonitrile (CH$_3$CN), methylene chloride (DCM), chloroform (CHCl$_3$), dimethyl formamide (DMF) or mixtures thereof. Suitable bases include dimethylaminopyridine (DMAP), diisopropylethylamine, pyridine, triethylamine, KOH, potassium t-butoxide and NaOH etc. The reactions are usually carried out at a temperature of from about 0° C. up to about 22° C. (room temperature).

More specifically, one method of forming the high molecular weight polymer conjugates includes:

1) reacting an amine protected activated polymeric residue of the formula:

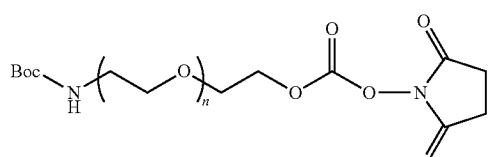

wherein n is a positive integer,
with a heterobifunctional polymeric residue of the formula:

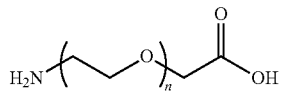

wherein n is a positive integer,
to form a compound of the formula:

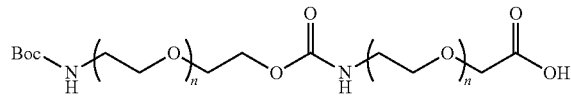

2) reacting the intermediate from step 1) with an activating group, biologically active moiety, diagnostic agent or terminal group to form a compound of the formula:

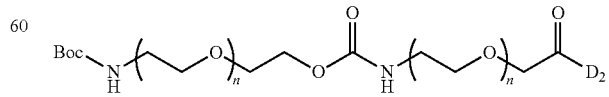

wherein $D_2$ is an activating group, biologically active moiety, diagnostic agent or terminal group such as, for example, ala-camptothecin:

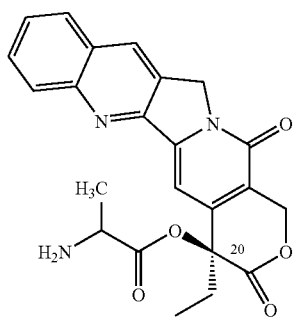 [SMILES: CC[C@@]1(OC(=O)C(C)N)C(=O)OCc2c1cc1n(c2=O)Cc2cc3ccccc3nc2-1]

3) deprotecting the amine portion and activating it with a moiety such as maleimide to form a compound of the formula:

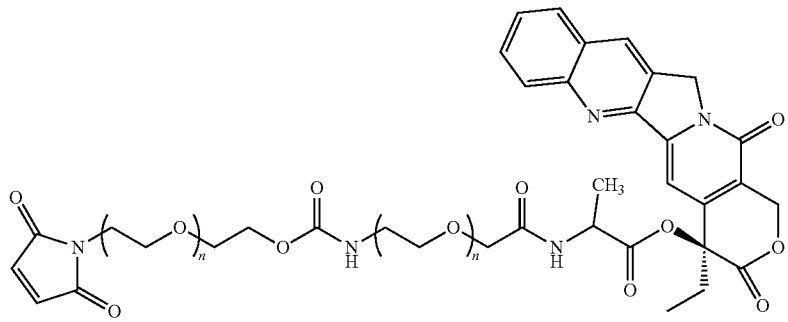

The foregoing shows an activated carbonate which yields the hetero-bifunctional with a carbamate linkage. As will be appreciated by those of ordinary skill, an activated ester could be used the outset of the process to form the amide linkage.

One skilled in the art will appreciate that the conjugates prepared according to the methods of the present invention can increase in single or multiple polymer units thereby resulting in repeating the same or random polymer subunits depending on the methods chosen to achieve the desired conjugate.

Regardless of the route selected, some of the preferred compounds which result from the synthetic techniques described herein include:

4) and thereafter, reacting the maleimide intermediate with biologically active moiety such as a single chain antigen binding protein of the monoclonal antibody CC49 (which binds to TAG-72) or other fragment of either of the foregoing, all hereinafter designated "SCA" for convenience, to yield an SCA immunoconjugate of the formula:

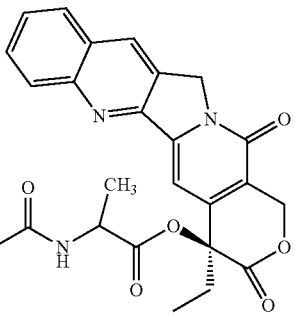

wherein n is a positive integer.

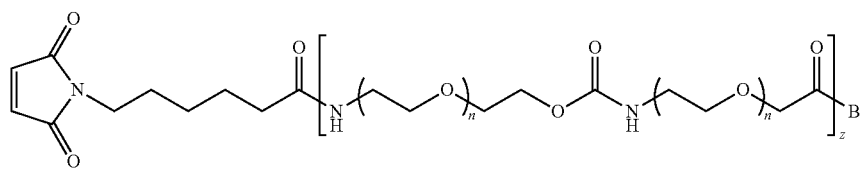
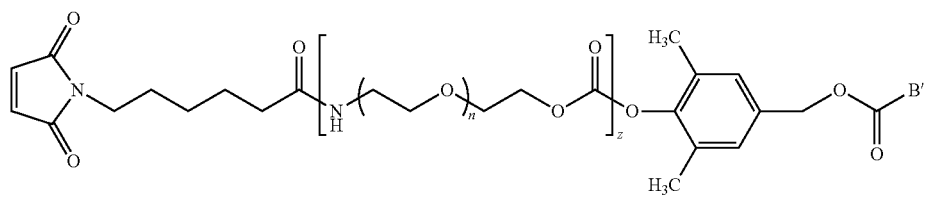
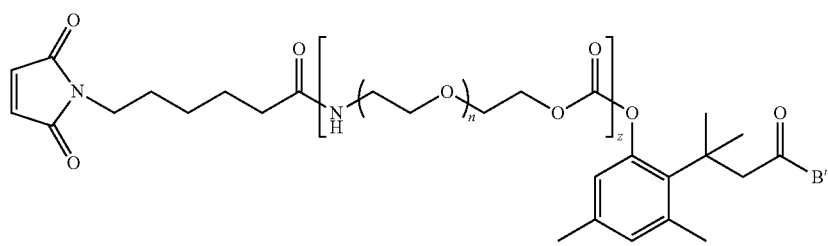
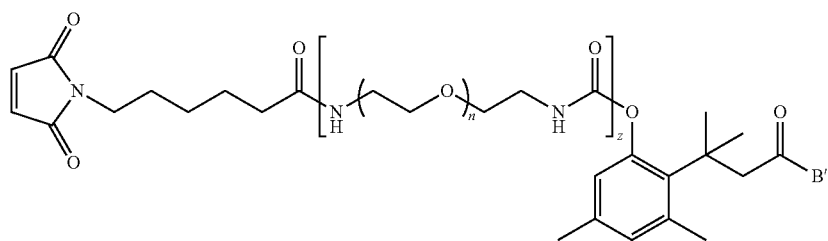
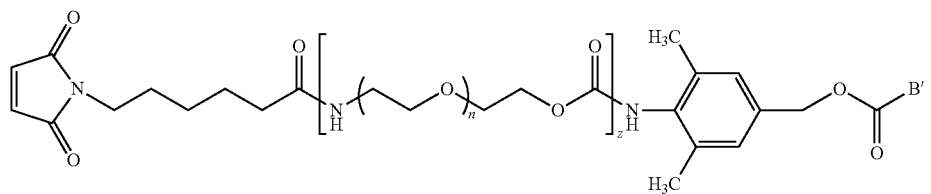
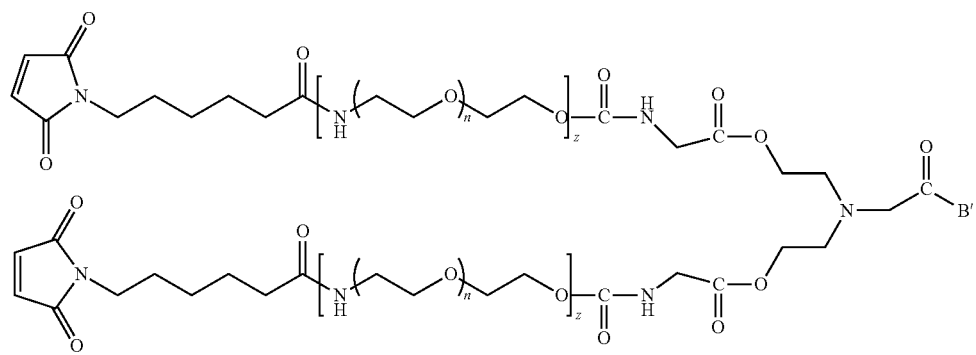

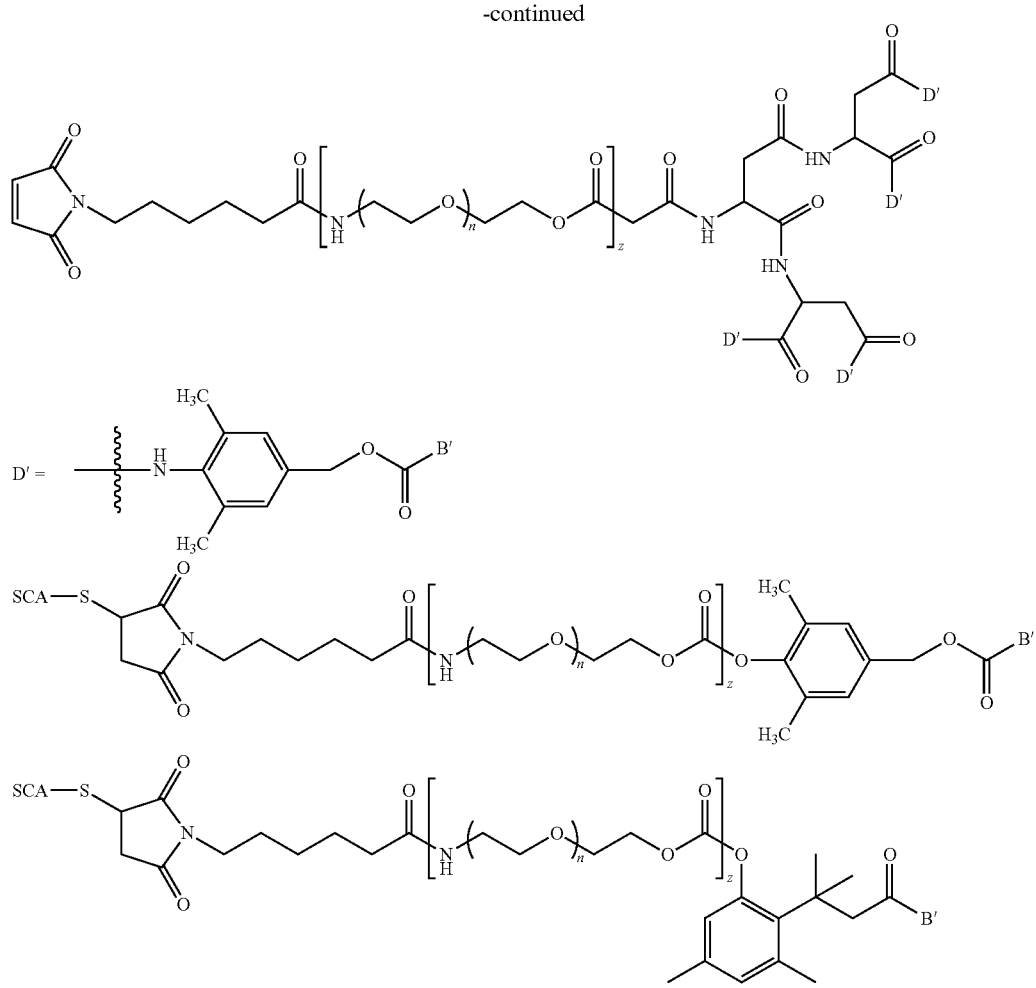
wherein, B and B' are leaving groups, activating agents, biologically active agents, diagnostic agents, etc. and SCA is a single chain-antibody.
Some other preferred compounds include:
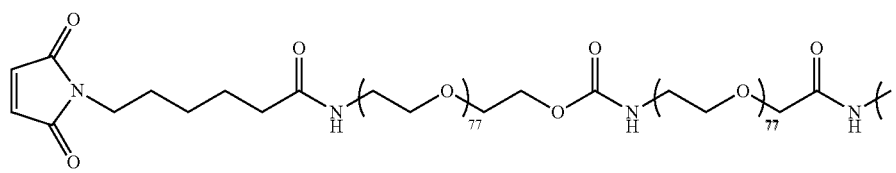
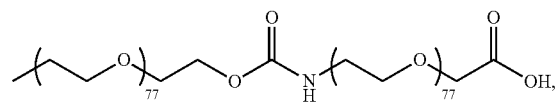
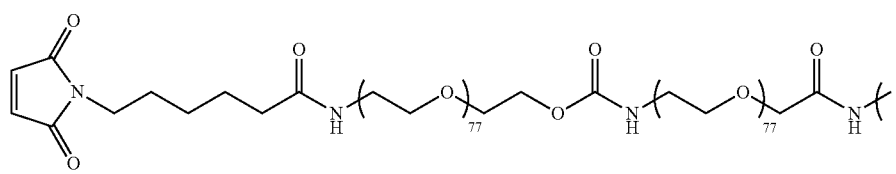

-continued
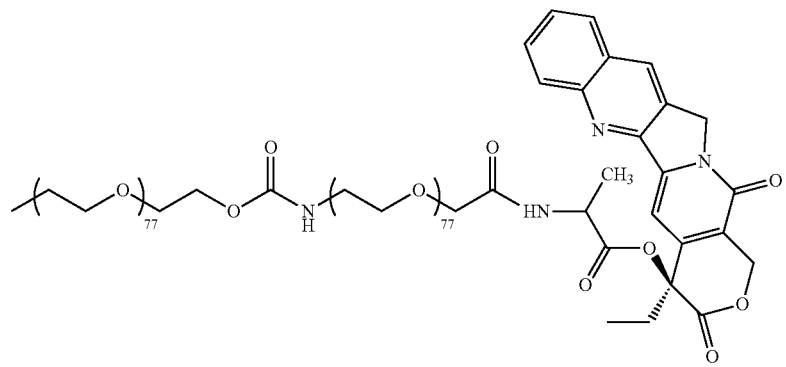
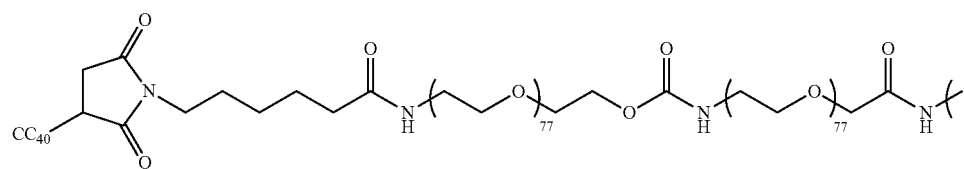
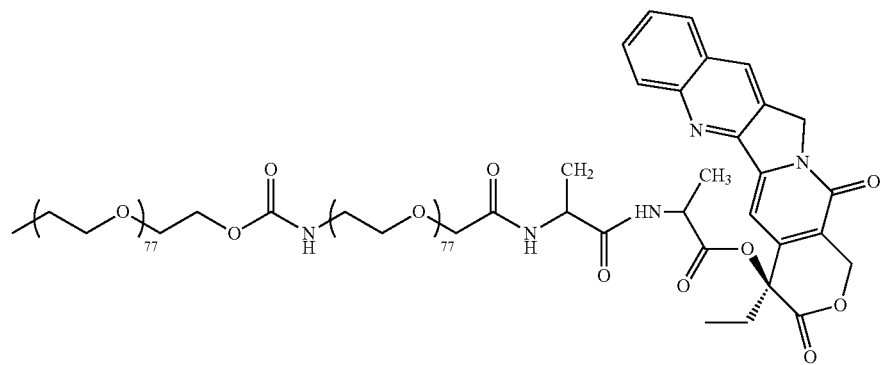
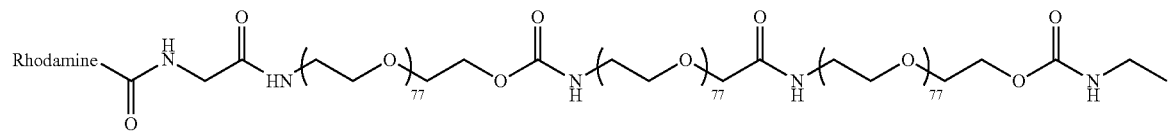
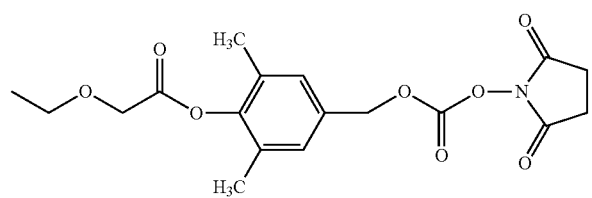
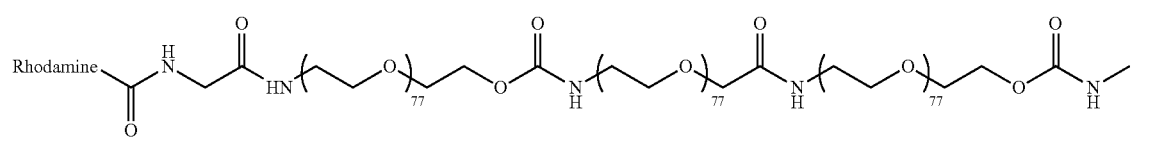
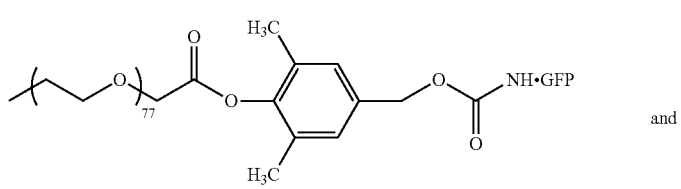
and

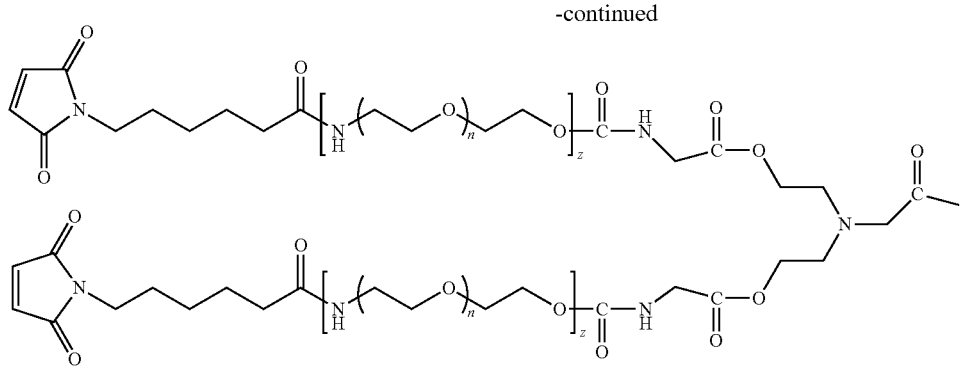

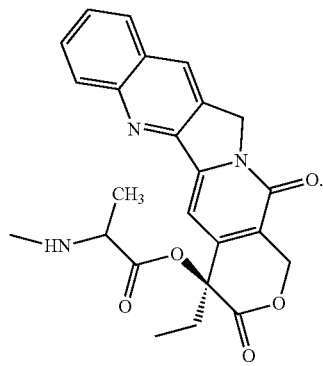

H. Methods of Treatment

Another aspect of the present invention provides methods of treatment for various medical conditions in mammals. The methods include administering to the mammal in need of such treatment, an effective amount of a heterobifunctional polymer composition of the invention, which has been prepared as described herein. The compositions are useful for, among other things, treating neoplastic disease, reducing tumor burden, preventing metastasis of neoplasms and preventing recurrences of tumor/neoplastic growths in mammals.

The amount of the compound administered will depend upon the parent molecule, e.g. peptide, polypeptide, protein, enzyme, small molecule drugs, etc. included therein. Generally, the amount of compound used in the treatment methods is that amount which effectively achieves the desired therapeutic result in mammals. Naturally, the dosages of the various compounds will vary somewhat depending upon the parent compound, rate of in vivo hydrolysis, molecular weight of the polymer, etc. Those skilled in the art will determine the optimal dosing of the compound selected based on clinical experience and the treatment indication. Actual dosages will be apparent to the artisan without undue experimentation.

The compounds of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the compounds are parenterally administered to mammals in need thereof.

EXAMPLES

The following examples serve to provide further appreciation of the invention but are not meant in any way to restrict the effective scope of the invention. The underlined and bold-faced numbers recited in the Examples correspond to those shown in the Schemes 1 to 9.

General Procedures

All reactions were ran under an atmosphere of dry nitrogen or argon. Commercial reagents were used without further purification. All PEG compounds were dried under vacuum or by azeotropic distillation from toluene prior to use. NMR spectra were obtained using a Varian Mercury® 300 NMR spectrometer and deuterated chloroform as the solvent unless otherwise specified. Chemical shifts ($\delta$) are reported in parts per million (ppm) downfield from tetramethylsilane (TMS).

HPLC method. The reaction mixtures and the purity of intermediates and final products were monitored by a Beckman Coulter System Gold® HPLC instrument employing a ZOBAX® 300 SB C-8 reversed phase column (150×4.6 mm) or a Phenomenex Jupiter® 300A C18 reversed phase column (150×4.6 mm) with a multiwavelength UV detector, using a gradient of 30-90% of acetonitrile in 0.5% trifluoroacetic acid (TFA) at a flow rate of 1 mL/min.

Compound 3. A solution of 1 (0.623 g, 0.180 mmol), 2 (0.623 g, 0.180 mmol), and N,N-dimethylaminopyridine (DMAP, 0.110 g, 0.90 mmol) in dichloromethane (DCM, 20 mL) was stirred at room temperature for 12 hrs. The solution was washed with 0.1 N HCl (2×20 mL), dried (MgSO$_4$), filtered, the solvent removed under reduced pressure, and crystallized from isopropyl alcohol (IPA, 25 mL) to give 3 (0.910 g, 0.134 mmol, 74.3%). $^{13}$C NMR (67.8 MHz, CDCl$_3$) $\delta$ 171.91, 155.79, 155.30, 66.15, 63.32, 40.34, 39.91, 34.26, 28.02.

Compound 4. A solution of 3 (0.707 g, 0.104 mmol) in DCM/trifluoroacetic acid (TFA) (8 mL:4 mL) was stirred at room temperature for 3.5 hrs at room temperature. The solvent was removed under reduced pressure and the resulting solid washed with either to yield 4 (0.707 g,). 104 mmol, ~100%). $^{13}$C NMR (67.8 MHz, CDCl$_3$) δ 172.18, 155.94, 66.62, 66.32, 63.49, 40.49, 39.71, 34.46.

Compound 5. To a solution of 3 (0.910 g, 0.134 mmol), 2-mercaptothiazoline (2-MT, 0.0319 g, 0.268 mmol), and DMAP (0.032.7 g, 0.268 mmol) in DCM (15 mL) cooled at 0° C. for 15 min was added 1-[3-(dimethylamino)-propyl]-3-ethylcarbodiimide hydrochloride (EDC, 0.0513 g, 0.268 mmol) and the reaction solution allowed to gradually warm to room temperature and then stirred for 12 hrs. The PEG derivative was precipitated with ethyl ether, collected by filtration, and crystallized from IPA (19 mL) to give 5 (0.820 g, 0.121 mmol, 90.0%). $^{13}$C NMR (67.8 MHz, CDCl$_3$) δ 200.94, 171.73, 155.85, 155.36, 65.75, 63.37, 55.54, 40.37, 39.94, 38.73, 28.08.

Compound 6. To a solution of 4 (0.668 g, 0.098 mmol) in DCM (15 mL) was added DMAP to adjust the pH to 7.0. Compound 5 (0.677 g, 0.098 mmol) was added and the reaction mixture stirred at room temperature for 12 hrs. The solution was washed with 0.1 N HCl (2×20 mL), dried (MgSO$_4$), filtered, solvent removed under reduced the pressure and residue crystallized from isopropyl alcohol (IPA, 25 mL) to give 6 (1.053 g, 0.077 mmol, 79.0%). $^{13}$C NMR (67.8 MHz, CDCl$_3$) δ 171.97, 170.72, 155.87, 155.36, 66.83, 66.24, 63.39, 40.40, 39.99, 38.74, 36.50, 34.34, 28.08.

Compound 8. To a solution of 6 (0.616 g, 0.045 mmol), 20-(S)-camptothecin alaninate trifluoroacetic acid salt (0.0706 g, 0.136 mmol), and DMAP (0.111 g, 0.906 mmol) in DCM (10 mL) cooled at 0° C. for 15 min was added EDC (0.026 g, 0.136 mmol) and the reaction solution allowed to warm to room temperature. After stirring for 12 hrs, the solution was washed with 0.1 N HCl (2×20 mL), dried (MgSO$_4$), filtered, the solvent removed under reduced pressure, and the residue crystallized from isopropyl alcohol (IPA, 13 mL) to give 8 (0.536 g, 0.038 mmol, 85.0%). $^{13}$C NMR (67.8 MHz, CDCl$_3$) δ 171.09, 170.83, 170.63, 166.48, 156.82, 155.99, 151.82, 148.46, 146.01, 144.98, 130.77, 130.12, 129.40, 128.06, 127.77, 127.58, 119.72, 95.58, 66.77, 66.77, 63.57, 49.74, 47.56, 40.55, 40.14, 38, 90, 36.70, 36.41, 31.48, 28.22, 17.58, 7.40.

Compound 9. A solution of 8 (0.536 g, 0.038 mmol) in DCM/TFA (8 mL:4 mL) was stirred at room temperature for 2 hrs. The solvent was removed under reduced pressure and the residue washed with ethyl ether to give 9 (0.536 g, 0.038 mmol, ~100%). $^{13}$C NMR (67.8 MHz, CDCl$_3$) δ 170.99, 170.81, 170.60, 166.25, 156.58, 155.79, 151.56, 148.19, 145.79, 144.79, 130.71, 129.92, 129.12, 127.91, 127.63, 127.37, 119.46, 95.44, 66.71, 66.54, 63.34, 49.59, 47.45, 40.34, 39.59, 38, 78, 36.34, 36.08, 31.24, 17.24, 7.20.

Compound 11. To a solution of 9 (0.818 g, 0.059 mmol) in DCM (15 mL) was added DMAP to adjust the pH to 7.0, then 10 was added and the solution cooled to 0° C. 1,3-diisopropylcarbodiimide (DIPC, 0.0554 μL, 0.354 mmol) was added to the reaction and the mixture allowed to warm to room temperature with stirring for 12 hrs. The solution was washed with 0.1 N HCl (2×20 mL), dried (MgSO$_4$), filtered, the solvent removed under reduced pressure and the residue crystallized from isopropyl alcohol (IPA, 16 mL) to give 11 (0.65 g, 0.046 mmol, 78%). $^{13}$C NMR (67.8 MHz, CDCl$_3$) δ 172.22, 171.10, 170.84, 170.60, 170.32, 166.48, 156.83, 155.99, 151.82, 148.48, 146.04, 144.98, 133.70, 130.76, 130.13, 129.43, 128.06, 127.78, 127.60, 119.75, 95.56, 66.99, 66.77, 63.58, 49.74, 47.56, 40.57, 38.92, 37.39, 36.72, 36.43, 36.05, 31.48, 28.08, 26.17, 25.18, 24.86, 17.30, 7.40.

Compound 12. A. Reduction of protein CC49: to a solution of 28 mg (2.79 mg/ml) of CC49 in 100 mM sodium phosphate, pH 7.8, at 37° C., 2 mM EDTA was added with 2 mM DTT and reaction allowed to proceeded for 2 hrs. The DTT was removed by a desalting column equilibrated with a solution of 100 mM sodium phosphate, pH 6.5, and 2 mM EDTA. The final concentration of the reduced protein was 0.39 mg/ml (~23 mg, ~60 ml, 83%).

B. PEGylation: CC49 and 11 were mixed at 1:10 molar ratio in a solution of 100 mM sodium phosphate, pH 6.5, 2 mM EDTA and reacted at 25° C. for 2 hrs.

C. Purification of CC49-PEG-CPT: the pH value of the reaction solution was adjusted to 5 with HOAc and water (~200 mL) was added to reduce the conductivity of the solution to less than 2 mS and the mixture loaded onto a Poros HS column at 5 mL/min. The product was eluted by 1 M NaCl in 10 mM sodium phosphate solution and the fractions of protein peak were combined and concentrated using a 30 k Centriplus centrifuge tube. The concentrated sample was dialyzed against saline and analyzed for active component. An iodine stain test found no non-protein conjugated PEG species in the product.

Compound 13. A solution of 6 (4.50 g, 0.335 mmol) in DCM/TFA (30 mL: 15 mL) was stirred at room temperature for 3.5 hrs at room temperature. The solvent was then removed under reduced pressure and the resulting solid washed with ether to yield 13 (4.30 g, 0.320 mmol, 95.6%). $^{13}$C NMR (67.8 MHz, CDCl$_3$) δ 171.59, 155.58, 66.36, 65.89, 63.02, 40.05, 39.36, 38.61, 35.85, 33.96.

Compound 14. To a solution of 13 (4.30 g, 0.320 mmol) in DCM (50 mL) was added DMAP to pH 7.0. Then compound 5 (2.20 g, 0.320 mmol) was added and the reaction mixture stirred at room temperature for 12 hrs. The solution was washed with 0.1 N HCl (2×30 mL), dried (MgSO$_4$), filtered, the solvent removed under reduced pressure and the residue crystallized from isopropyl alcohol (IPA, 25 mL) to give 14 (5.30 g, 0.260 mmol, 81.2%). $^{13}$C NMR (67.8 MHz, CDCl$_3$) δ 171.77, 170.60, 155.75, 66.73, 66.12, 63.28, 40.29, 39.86, 38.66, 36.41, 34.19, 27.99.

Compound 15. A solution of 14 (5.30 g, 0.260 mmol) in DCM/TFA (30 mL:15 mL) was stirred at room temperature for 3.5 hrs at room temperature. The solvent was then removed under reduced pressure and the resulting solid washed with ether to yield 15 (5.30 g, 0.260 mmol, ~100%). $^{13}$C NMR (67.8 MHz, CDCl$_3$) δ 171.77, 170.60, 155.75, 66.73, 66.12, 63.28, 40.29, 39.86, 38.66, 36.41, 34.19.

Compound 18. To a solution of Rhodamine B base (1.00 g, 2.09 mmol), Glycine t-butylester hydrochloride salt (0.670 g, 4.0 mmol) and DMAP (0.767 g, 8.0 mmol) in DCM (30 mL) cooled to 0° C. for 15 min was added EDC (0.767 g, 4.0 mmol). The reaction mixture was allowed to warm to room temperature and stirred for 12 hrs. The solution was washed with 0.1 N HCl (2×30 mL), dried (MgSO$_4$), filtered, solvent removed under reduced pressure and the residue purified by silica gel column chromatography using hexane and ethyl acetate (3:2, v/v) as eluting solvents to give 18 (0.937 g, 1.58 mmol, 76%). $^{13}$C NMR (67.8 MHz, CDCl$_3$) δ 167.30, 166.73, 153.06, 153.01, 148.36, 132.05, 130.60, 129.31, 127.63, 123.46, 122.67, 107.64, 104.69, 97.21, 80.80, 64.74, 44.10, 42.03, 27.63, 12.41.

Compound 19. A solution of 18 (0.937 g, 1.58 mmol) in DCM/TFA (16 mL:8 mL) was stirred at room temperature for 2 hrs. The solvent was removed under reduced pressure and the residue washed by ethyl ether to give 19 (0.930 g, 1.57 mmol, ~100%).

$^{13}$C NMR (67.8 MHz, CDCl$_3$) δ 169.30, 167.83, 152.72, 152.15, 144.14, 133.09, 130.28, 128.83, 123.64, 123.41, 112.32, 103.89, 64.69, 48.47, 41.49, 11.44.

Compound 20. To a solution of 19 (0.421 g, 0.785 mmol), 2-MT (0.140 g, 1.18 mmol), and DMAP (0.287 g, 2.30 mmol) in DCM (15 mL) cooled at 0° C. for 15 min was added EDC (0.226 g, 1.18 mmol) and the reaction solution allowed to gradually warm to room temperature and then stirred for 12 hrs. The solution was washed with 0.1 N HCl (2×20 mL), dried (MgSO$_4$), filtered, the solvent removed under reduced pressure to give 20 (0.450 g, 0.706 mmol, 90%). $^{13}$C NMR (67.8 MHz, CDCl$_3$) δ 200.68, 168.90, 167.73, 153.27, 152.07, 148.10, 139.66, 132.47, 130.20, 129.39, 127.94, 123.63, 122.85, 108.19, 98.14, 65.11, 55.77, 51.31, 45.68, 44.68, 33.67, 29.09, 12.53.

Compound 21. To a solution of 15 (2.7 g, 0.134 mmol) in DCM was added DMAP to adjust the pH to 7. Compound 20 (171 mg, 0.268 mmol) was added and the reaction solution was stirred at room temperature for 12 hrs. The reaction mixture was washed with 0.1N HCl, the solvent evaporated under reduced pressure, and the solid crystallized from IPA to yield 21 (2.3 g, 0.112 mmol, 84%). $^{13}$C NMR (67.8 MHz, CDCl$_3$) δ 201.00, 170.78, 167.73, 155.88, 152.86, 148.80, 132.51, 129.86, 128.06, 127.87, 123.59, 122.53, 108.14, 98.09, 66.86, 63.45, 55.57, 44.37, 43.99, 40.43, 38.80, 38.54, 36.57, 34.32, 28.10, 12.18.

Compound 22. To a solution of 21 (2.3 g, 0.112 mmol), 2-MT (0.027 g, 0.224 mmol), and DMAP (0.027 g, 0.224 mmol) in DCM (1, mL) cooled at 0 G was added EDC (0.043 g, 0.224 mmol). The reaction solution was gradually warmed to room temperature and stirred for 12 hrs. The PEG derivative was precipitated with ethyl ether, filtered, and crystallized from IPA to give 22 (2.0 g, 0.097 mmol, 86%). $^{13}$C NMR (67.8 MHz, CDCl$_3$) δ 200.00, 171.70, 170.64, 167.96, 167.68, 155.79, 152.86, 148.24, 132.38, 129.86, 127.84, 127.72, 123.55, 122.38, 104.12, 97.47, 66.80, 63.37, 55.51, 44.91, 40.37, 38.72, 38.44, 36.50, 28.08, 12.26.

Compound 23. A solution of 22 (2.0 g, 0.097 mmol), 3,5-dimethyl-4-hydroxybenzyl alcohol (0.059 g, 0.388 mmol), and DMAP (0.048 g, 0.388 mmol) in DCM (10 mL) was refluxed for 12 hrs. The PEG derivative was precipitated with ethyl ether, filtered, and crystallized from IPA to give 23 (1.9 g, 0.096 mmol, 99%). δ 170.40, 168.40, 167.64, 167.38, 155.59, 152.65, 148.01, 132.13, 129.66, 129.11, 127.66, 126.16, 123.31, 122.14, 107.48, 103.99, 97.26, 66.88, 63.34, 43.70, 40.15, 38.52, 38.25, 36.26, 34.37, 15.76, 12.07.

Compound 24. To a solution of 23 (1.9 g, 0.097 mmol) and N,N'-disuccinimidyl carbonate (0.199 g, 0.775 mmol) in DCM (20 mL) and DMF (2 mL) cooled to 0° C. was added pyridine (0.063 μL, 0.775 mol). The reaction solution was gradually warmed to room temperature and stirred for 12 hrs. The PEG derivative was precipitated with ethyl ether, filtered, and crystallized from IPA to give 24 (1.58 g, 0.075 mmol, 77%).

$^{13}$C NMR (67.8 MHz, CDCl$_3$) δ 171.22, 170.49, 168.35, 168.05, 167.73, 167.47, 155.65, 152.71, 148.07, 132.24, 129.69, 128.09, 127.72, 123.39, 122.23, 107.53, 104.02, 97.30, 66.65, 63.19, 43.77, 40.22, 38.57, 38.31, 36.22, 34.43, 24.89, 15.79, 12.13.

Compound 25. Activated PEG linker 24 was added to a solution of GFP (2 mg/ml) in 0.05 M HEPES, pH 7.8, with a molar ratio of 30:1 (PEG:GFP). The solution was stirred at 25° C. under N$_2$ for 45 min, the pH of the solution was lowered by adding sodium phosphate buffer, pH 6.4, to a final concentration of 50 mM. The free PEG was removed on a Superdex 200 Hiload 16/60 column (Amersham Pharmacia Biotech, Piscataway, N.J.) using a Biocad Perfusion Chromatography Workstation. The elution buffer was comprised of 10 mM sodium phosphate, pH 6.8 and 150 mN NaCl. The fractions that exhibited both absorbance: at 280 nm and fluorescence were pooled and concentrated using ultrafree-15 centrifugal filter device with 30 k NMWL membrane (Millipore Corp., Bedford, Mass.). The PEG-GFP (25) concentration was determined by UV at 489 nm using an extinction coefficient of 55,000 cm$^{-1}$ M$^{-1}$.

Compound 27. To a solution of 6, 26, and DMAP in DCM is added EDC and the solution stirred at room temperature for 12 hrs. The solvent is removed under reduced pressure and the solid crystallized from IPA to give 27. The structure of 27 is confirmed by $^{13}$C NMR.

Compound 28. A solution of 27 in DCM/TFA is stirred at room temperature for 12 hrs. The solvent is removed under reduced pressure and the solid crystallized from IPA to give 28. The structure of 28 is confirmed by $^{13}$C NMR.

Compound 29. To a solution of 10, 2-MT, and DMAP in DCM cooled at 0° C. for 15 min is added EDC and the reaction solution allowed to gradually warm to room temperature and then stirred for 2 hrs. The solution is then washed by 0.1 N HCl, dried (MgSO4), and the solvent removed under reduced pressure to give 29. The structure of 29 is confirmed by $^{13}$C NMR.

Compound 30. A solution of 28, 29 and DMAP in DCM is stirred at room temperature for 12 hrs. The solvent is removed under reduced pressure and the solid crystallized from IPA to give 30. The structure of 30 is confirmed by $^{13}$C NMR.

Compound 31. To a solution of 30, 7, and DMAP in DCM cooled at 0° C. for 15 min is added EDC and the reaction solution allowed to warm to room temperature. After stirring for 12 hrs, the solution is washed with 0.1 N HCl, dried (MgSO$_4$), filtered, the solvent removed under reduced pressure, and the residue crystallized from IPA to give 31. The structure of 31 is confirmed by $^{13}$C NMR.

What we claim:
1. A compound of the formula:

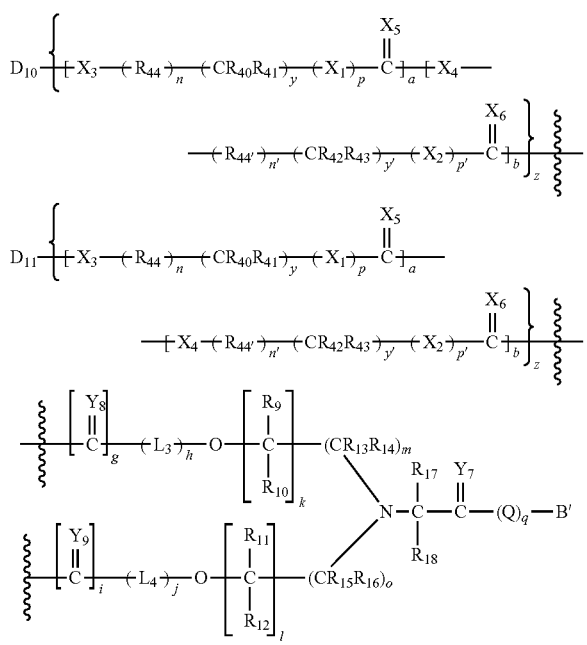

wherein:

$X_1$-$X_6$ are independently O, S or $NR_1$;

$R_{44}$ and $R_{44'}$ are independently selected polyalkylene oxides;

$R_1$ is selected from the group consisting of hydrogen, $C_{1-6}$ alkyls, $C_{3-12}$ branched alkyls, $C_{3-8}$ cycloalkyls, $C_{1-6}$ substituted alkyls, aralkyls, and $C_{3-8}$ substituted cycloalkyls;

$R_{40-43}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

y and y' are independently zero or a positive integer;

p and p' are independently zero or one n and n' are independently a positive integer;

a and b are independently zero or a positive integer, provided that a+b is greater than or equal to 2;

z is a positive integer;

$D_{10}$ and $D_{11}$ are independently selected from the group consisting of OH, halogens, drugs, enzymes, proteins, therapeutically active compounds, dyes, chelating agents', isotope labeled compounds;

$Y_{7-9}$ are independently selected from the group consisting of O, S $NR_{1''}$;

$R_{1''}$ is hydrogen or methyl;

$R_{9-18}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$L_{3-4}$ are independently selected bifunctional linkers;

Q is selected from the group consisting of -$L_5$-C(=$Y_{10}$)— wherein $L_5$ is the same group that defines $L_{3-4}$ and $Y_{10}$ is the same group that defines $Y_{7-9}$, hydrophobic moieties, bifunctional linking moieties and combinations thereof;

l, k, m and o are independently positive integers;

j and h are independently zero or a positive integer;

g, i and q are independently zero or one; and

B' is selected from the group consisting of leaving groups, activating groups, OH, biologically active moieties and diagnostic agents.

2. The compound of claim 1, having the formula

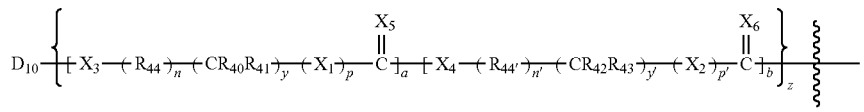

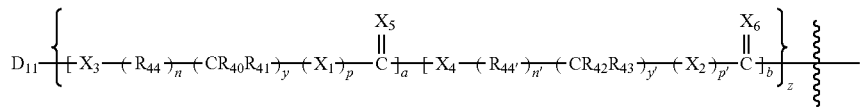

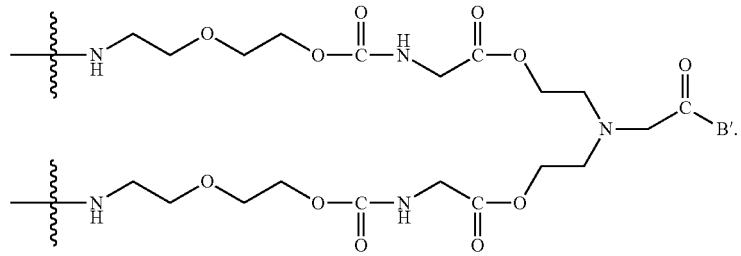

3. The compound of claim 2, selected from the group consisting of:

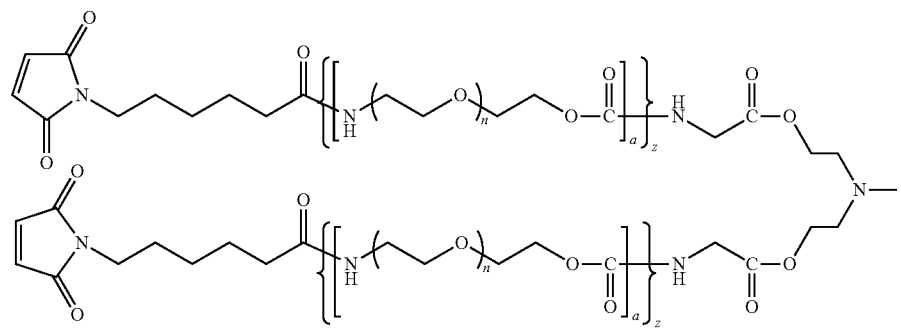

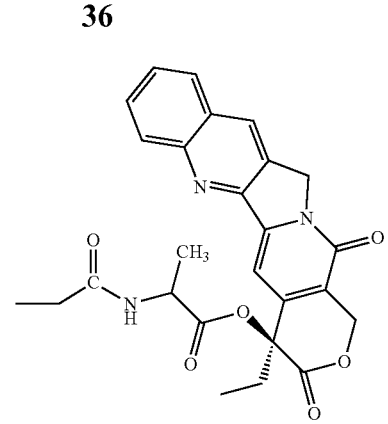

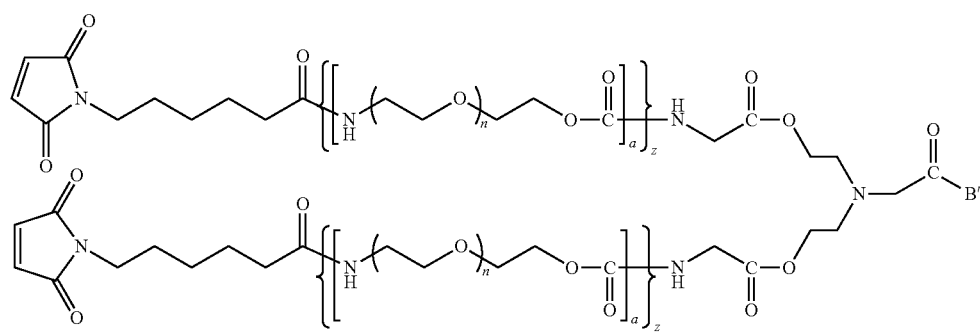

wherein,

B' is selected from the group consisting of leaving groups, activating agents, OH, biologically active agents, and diagnostic agents.

4. The compound of claim 3, wherein B' is selected from the group consisting of maleimide and residues of hydroxyl-containing or amine-containing compounds, wherein there is at least one hydroxyl or amine available in the hydroxyl- or amine-containing compounds which can react and link with the polymeric conjugate.

5. The compound of claim 3, wherein B' is selected from the group consisting of anthracyclines, daunorubicin, doxorubicin, p-hydroxyaniline mustard, cytosine, ara-C, gemcitibine, camptothecin, vancomycin, paullones, paclitaxel, cisplatin, vincristine and vinblastine.

* * * * *